US006994848B2

(12) United States Patent
Hsu et al.

(10) Patent No.: US 6,994,848 B2
(45) Date of Patent: Feb. 7, 2006

(54) LACTOBACILLUS PARACASEI STRAIN GM-080 FOR TREATING ALLERGY RELATED DISEASES

(75) Inventors: Ching-Hsiang Hsu, Tainan (TW); Wei-Chih Su, Tainan (TW); Ying-Yu Wang, Tainan (TW); Tzu-Chi Chang, Tainan (TW); Cheng-Wei Lai, Tainan (TW)

(73) Assignee: GenMont Biotech Inc., (TW)

( * ) Notice: Subject to any disclaimer, the term of this patent is extended or adjusted under 35 U.S.C. 154(b) by 65 days.

(21) Appl. No.: 10/808,503

(22) Filed: Mar. 25, 2004

(65) Prior Publication Data

US 2005/0214271 A1    Sep. 29, 2005

(51) Int. Cl.
A01N 63/00    (2006.01)
C12N 1/00    (2006.01)
C12N 1/20    (2006.01)

(52) U.S. Cl. .............................. 424/93.45; 435/252.9; 435/853

(58) Field of Classification Search ................ 435/243, 435/252.1, 252.9, 853; 424/93.45
See application file for complete search history.

(56) References Cited

U.S. PATENT DOCUMENTS 5,556,785 A    9/1996    Kishida
6,225,332 B1    5/2001    Miller et al.
2002/0031503 A1    3/2002    Gill et al.

OTHER PUBLICATIONS

Blease et al. "Chemokines and their role in airway hyper-reactivity." *Respir Res* 2000;1:54-61.
Sareneva T et al. "Influenza A virus-induced IFN-/□/□ and IL-18 synergistically enhance IFN-□ gene expression in human T cells." *J Immunol* 1998; 160-6032-6038.
Shida K et al. "*Lactobacillus casei* inhibits antigen-induced IgE secretion through regulation of cytokine production in murine splenocyte cultures." *Int Arch Allergy Immunol* 1998; 115:278-287.
Contractor NV et al. "Lymphoid hyperplasia, autoimmunity and compromised intestinal intraepithelial lymphocyte development in colitis-free gnotobiotic IL-2-deficient mice." *J Immunol* 1998; 160:385-394.
Hessle et al. "Lactobacilli from human gastrointestinal mucosa are strong stimulators of IL-12 production." *Clin Exp Immunol* 1999; 116:276-282.
Gardiner, G. et al, "Development of a probiotic cheddar cheese containing human-derived *Lactobacillus paracasei* strains." *Appl Environ Microbiol.* 1998; 64: 2192-2199.
Angelis, M. et al. "Characterization of non-starter lactic acid bacteria from Italian ewe cheeses based on phenotypic, genotypic, and cell wall protein analyses." *Appl Environ Microbiol.* 2001; 67: 2011-2020.
Atanassova, M. et al. "Isolation and partial biochemical characterization of a proteinaceous anti-bacteria and anti-yeast compound produced by *Lactobacillus paracasei* subsp. paracasei strain M3." *Int. J. Food Microiobiol.* 2003; 87: 63-73.
Ocaña, V. S. et al. "Growth inhibition of *Staphylococcus aureus* by $H_2O_2$-producing *Lactobacillus paracasei* subsp. paracasei isolated from the human vagina." *FEMS Immunol. Med. Microbiol.* 1999; 23: 87-92.
Sookkhee S. et al. "Lactic acid bacterial form healthy oral cavity of Thai volunteers: inhibition of oral pathogens." *Journal of Applied Microbiology* 2001; 90:172-179.
Ward, L.J.H. and Timmins, M.J. (1999) "Differentiation of *Lactobacillus casei*, *Lactobacillus paracasei* and *Lactobacillus rhamnosus* by polymerase chain reaction." *Lett. Appl. Microbiol.* 29: 90-92.
Caridl, A. "Selection of *Escherichia coli*-inhibiting strains of *Lactobacillus paracasei* subsp. paracasei." *Journal of Industrial Microbiology & Biotechnology* 2002; 29: 303-308.
Jacobsen, C. N. et al., "Screening of probiotic activities of forty-seven strains of *Lactobacillus* spp. by in vitro techniques and evaluation of the colonization ability of five selected strains in human." *Appl. Environ. Microbiol.* 1999; 65: 4949-4956.

*Primary Examiner*—David M. Naff
*Assistant Examiner*—Deborah K. Ware
(74) *Attorney, Agent, or Firm*—Banner & Witcoff, Ltd.

(57) ABSTRACT

The present invention provides an isolated microorganism strain, *Lactobacillus paracasei* GM-080, which is found to be effective in treating allergy. The use of the *Lactobacillus paracasei* GM-080 in treating allergy related disease is also provided.

21 Claims, 14 Drawing Sheets

```
                1                                                          60
CCRC12913   (1) ------------------------------------------------------------
CCRC14001   (1) ------------------------------------------------------------
  GM-080    (1) ------------------------------------------------------------
CCRC16100   (1) ------------------------------------------------------------
    KLB58   (1) ----------------AACGCTG-CAGCGTGCCCTA-TACATGCCAGTCGAACGAGTTCTC
      PB4   (1) ATCCTGGCTCAGGATGAACGCTGGCGGCGTGCCTAATACATGCAAGTCGAACGAGTTCTC
      F31   (1) ----------------AACGCTGGCGGCGTGCCTAATACATGCAAGTCGAACGAGTTCTC
Consensus   (1)

61                                                          120
CCRC12913   (1) ------------------------------------------------------------
CCRC14001   (1) -----------------------------------------------------GGTGAGTAC
  GM-080    (1) ------------------------------------------------------GTGAGTAC
CCRC16100   (1) --------------------------------------------------GCGAGGGTGAGTAC
    KLB58  (43) GTTGATGATCCGTGCTTGCACCGAGATTCAACATGGAACGAGTGGCGGACGGGTGAGTAA
      PB4  (61) GTTGATGATCCGTGCTTGCACCGAGATTCAACATGGAACGAGTGGCGGACGGGTGAGTAA
      F31  (45) GTTGATGATCCGTGCTTGCACCGAGATTCAACATGGAACGAGTGGCGGACGGGTGAGTAA
Consensus  (61)                                                 G   GGGTGAGTA 121                                                        180
CCRC12913   (1) ----TGGGTA-CCTGCCCCTTAAGTGGGGGATAACATTTGGAAACAGATGCTAATACCGCA
CCRC14001  (10) C--GTGGGTA-CCTGCCCCTTAAGTGGGGGATAACATTTGGAAACAGATGCTAATACCGCA
  GM-080   (9)  C--GTGGGTA-CCTGCCCCTTA-GTGGGGGATAACATTTGGAAACAGATGCTAATACCGCA
CCRC16100  (15) C--GTGGGTA-CCTGCCCCTTAAGTGGGGGATAACATTTGGAAACAGATGCTAATACCGCA
    KLB58 (103) CACGTGGGTAACCTGCCCCTTAAGTGGGGGATAACATTTGGAAACAGATGCTAATACCGCA
      PB4 (121) CACGTGGGTAACCTGCCCCTTAAGTGGGGGATAACATTTGGAAACAGATGCTAATACCGCA
      F31 (105) CACGTGGGTAACCTGCCCCTTAAGTGGGGGATAACATTTGGAAACAGATGCTAATACCGCA
Consensus (121) C  GTGGGTA CCTGCCCCTTAAGTGGGGGATAACATTTGGAAACAGATGCTAATACCGCA 181                                                        240
CCRC12913  (56) TAGATCCAAGAACCGCATGGTTCTTGGCTGAAAGATGGCGTAAGCTATCGCTTTTGGATG
CCRC14001  (67) TAGATCCAAGAACCGCATGGTTCTTGGCTGAAAGATGGCGTAAGCTATCGCTTTTGGATG
  GM-080   (65) TAGATCCAAGAACCGCATGGTTCTTGGCTGAAAGATGGCGTAAGCTATCGCTTTTGGATG
CCRC16100  (72) TAGATCCAAGAACCGCATGGTTCTTGGCTGAAAGATGGCGTAAGCTATCGCTTTTGGATG
    KLB58 (163) TAGATCCAAGAACCGCATGGTTCTTGGCTGAAAGATGGCGTAAGCTATCGCTTTTGGATG
      PB4 (181) TAGATCCAAGAACCGCATGGTTCTTGGCTGAAAGATGGCGTAAGCTATCGCTTTTGGATG
      F31 (165) TAGATCCAAGAACCGCATGGTTCTTGGCTGAAAGATGGCGTAAGCTATCGCTTTTGGATG
Consensus (181) TAGATCCAAGAACCGCATGGTTCTTGGCTGAAAGATGGCGTAAGCTATCGCTTTTGGATG 241                                                        300
CCRC12913 (116) GACCCGCGGCGTATTAGCTAGTTGGTGAGGTAATGGCTCACCAAGGCGATGATACGTAGC
CCRC14001 (127) GACCCGCGGCGTATTAGCTAGTTGGTGAGGTAATGGCTCACCAAGGCGATGATACGTAGC
  GM-080  (125) GACCCGCGGCGTATTAGCTAGTTGGTGAGGTAATGGCTCACCAAGGCGATGATACGTAGC
CCRC16100 (132) GACCCGCGGCGTATTAGCTAGTTGGTGAGGTAATGGCTCACCAAGGCGATGATACGTAGC
    KLB58 (223) GACCCGCGGCGTATTAGCTAGTTGGTGAGGTAATGGCTCACCAAGGCGATGATACGTAGC
      PB4 (241) GACCCGCGGCGTATTAGCTAGTTGGTGAGGTAATGGCTCACCAAGGCGATGATACGTAGC
      F31 (225) GACCCGCGGCGTATTAGCTAGTTGGTGAGGTAATGGCTCACCAAGGCGATGATACGTAGC
Consensus (241) GACCCGCGGCGTATTAGCTAGTTGGTGAGGTAATGGCTCACCAAGGCGATGATACGTAGC 301                                                        360
CCRC12913 (176) CGAACTGAGAGGTTGATCGGCCACATTGGGACTGAGACACGGCCCAAACTCCTACGGGAG
CCRC14001 (187) CGAACTGAGAGGTTGATCGGCCACATTGGGACTGAGACACGGCCCAAACTCCTACGGGAG
  GM-080  (185) CGAACTGAGAGGTTGATCGGCCACATTGGGACTGAGACACGGCCCAAACTCCTACGGN--
CCRC16100 (192) CGAACTGAGAGGTTGATCGGCCACATTGGGACTGAGACACGGCCCAAACTCCTACGGG--
    KLB58 (283) CGAACTGAGAGGTTGATCGGCCACATTGGGACTGAGACACGGCCCAAACTCCTACGGG--
      PB4 (301) CGAACTGAGAGGTTGATCGGCCACATTGGGACTGAGACACGGCCCAAACTCCTACGGG--
      F31 (285) CGAACTGAGAGGTTGATCGGCCACATTGGGACTGAGACACGGCCCAAACTCCTACGGG--
Consensus (301) CGAACTGAGAGGTTGATCGGCCACATTGGGACTGAGACACGGCCCAAACTCCTACGGG
```

FIG. 3

```
                    361                                                      420
CCRC12913   (236) GGCCAGCAGT-GGGAG---------------------------------------------
CCRC14001   (247) GGGCAGCAGT-GGGAG---------------------------------------------
GM-080      (243) GGGCAGCAGT-GGGA----------------------------------------------
CCRC16100   (250) AGGCAGCAGT-GGGA----------------------------------------------
KLB58       (341) AGGCAGCAGTAGGGAATCTTCCACAATGGACGCAAGTCTGATGGAGCAACGCCGCGTGAG
PB4         (359) AGGCAGCAGTAGGGAATCTTCCACAATGGACGCAAGTCTGATGGAGCAACGCCGCGTGAG
F31         (343) AGGCAGCAGTAGGGAATCTTCCACAATGGACGCAAGTCTGATGGAGCAACGCCGCGTGAG
Consensus   (361) AGGCAGCAGT GGGA 421                                                      480
CCRC12913   (251) ------------------------------------------------------------
CCRC14001   (262) ------------------------------------------------------------
GM-080      (257) ------------------------------------------------------------
CCRC16100   (264) ------------------------------------------------------------
KLB58       (401) TGAAGAAGGCTTTCGGGTCGTAAAACTCTGTTGTTGGAGAAGAATGGTCGGCAGAGTAAC
PB4         (419) TGAAGAAGGCTTTCGGGTCGTAAAACTCTGTTGTTGGAGAAGAATGGTCGGCAGAGTAAC
F31         (403) TGAAGAAGGCTTTCGGGTCGTAAAACTCTGTTGTTGGAGAAGAATGGTCGGCAGAGTAAC
Consensus   (421)

481                                                      540
CCRC12913   (251) ------------------------------------------------------------
CCRC14001   (262) ------------------------------------------------------------
GM-080      (257) ------------------------------------------------------------
CCRC16100   (264) ------------------------------------------------------------
KLB58       (461) TGTTGTCGGCGTGACGGTATCCAACCAGAAAGCCACGGCTAACTACGTGCCAGCAGCCGC
PB4         (479) TGTTGTCGGCGTGACGGTATCCAACCAGAAAGCCACGGCTAACTACGTGCCAGCAGCCGC
F31         (463) TGTTGTCGGCGTGACGGTATCCAACCAGAAAGCCACGGCTAACTACGTGCCAGCAGCCGC
Consensus   (481)

541                                                      600
CCRC12913   (251) ------------------------------------------------------------
CCRC14001   (262) ------------------------------------------------------------
GM-080      (257) ------------------------------------------------------------
CCRC16100   (264) ------------------------------------------------------------
KLB58       (521) GGTAATACGTAGGTGGCAAGCGTTATCCGGATTTATTGGGCGTAAAGCGAGCGCAGGCGG
PB4         (539) ------------------------------------------------------------
F31         (523) GGTAATACGTAGGTGGCAAGCGTTATCCGGATTTATTGGGCGTAAAGCGAGCGCAGGCGG
Consensus   (541)

601                                                      660
CCRC12913   (251) ------------------------------------------------------------
CCRC14001   (262) ------------------------------------------------------------
GM-080      (257) ------------------------------------------------------------
CCRC16100   (264) ------------------------------------------------------------
KLB58       (581) TTTTTTAAGTCTGATGTGAAAGCCCTCGGCTTAACCGAAGAAGCGCATCGGAAACTGGGA
PB4         (539) ------------------------------------------------------------
F31         (583) TTTTTTAAGTCTGATGTGAAAGCCCTCGGCTTAACCGAGGAAGCGCATCGGAAACTGGGA
Consensus   (601)

661                                                      720
CCRC12913   (251) ------------------------------------------------------------
CCRC14001   (262) ------------------------------------------------------------
GM-080      (257) ------------------------------------------------------------
CCRC16100   (264) ------------------------------------------------------------
KLB58       (641) AACTTGAGTGCAGAAGAGGACAGTGGAACTCCATGTGTAGCGGTGAAATGCGTAGATATA
PB4         (539) ------------------------------------------------------------
F31         (643) AACTTGAGTGCAGAAGAGGACAGTGGAACTCCATGTGTAGCGGTGAAATGCGTAGATATA
Consensus   (661)
```

FIG. 3 (continued)

|              |         | 721                                                          780 |
|--------------|---------|------------------------------------------------------------------|
| CCRC12913    | (251)   | ------------------------------------------------------------ |
| CCRC14001    | (262)   | ------------------------------------------------------------ |
| GM-080       | (257)   | ------------------------------------------------------------ |
| CCRC16100    | (264)   | ------------------------------------------------------------ |
| KLB58        | (701)   | TGGAAGAACACCAGTGGCGAAGGCGGCTGTCTGGTCTGTAACTGACGCTGAGGCTCGAAA |
| PB4          | (539)   | ------------------------------------------------------------ |
| F31          | (703)   | TGGAAGAACACCAGTGGCGAAGGCGGCTGTCTGGTCTGTAACTGACGCTGAGGCTCGAAA |
| Consensus    | (721)   |                                                              |

|              |         | 781                                                          840 |
|--------------|---------|------------------------------------------------------------------|
| CCRC12913    | (251)   | ------------------------------------------------------------ |
| CCRC14001    | (262)   | ------------------------------------------------------------ |
| GM-080       | (257)   | ------------------------------------------------------------ |
| CCRC16100    | (264)   | ------------------------------------------------------------ |
| KLB58        | (761)   | GCATGGGTAGCGAACAGGATTAGATACCCTGGTAGTCCATGCCGTAAACGATGAATGCTA |
| PB4          | (539)   | ------------------------------------------------------------ |
| F31          | (763)   | GCATGGGTAGCGAACAGGATTAGATACCCTGGTAGTCCATGCCGTAAACGATGAATGCTA |
| Consensus    | (781)   |                                                              |

|              |         | 841                                                          900 |
|--------------|---------|------------------------------------------------------------------|
| CCRC12913    | (251)   | ------------------------------------------------------------ |
| CCRC14001    | (262)   | ------------------------------------------------------------ |
| GM-080       | (257)   | ------------------------------------------------------------ |
| CCRC16100    | (264)   | ------------------------------------------------------------ |
| KLB58        | (821)   | GGTGTTGGAGGGTTTCCGCCCTTCAGTGCCGCAGCTAACGCATTAAGCATTCCGCCTGGG |
| PB4          | (539)   | ------------------------------------------------------------ |
| F31          | (823)   | GGTGTTGGAGGGTTTCCGCCCTTCAGTGCCGCAGCTAACGCATTAAGCATTCCGCCTGGG |
| Consensus    | (841)   |                                                              |

|              |         | 901                                                          960 |
|--------------|---------|------------------------------------------------------------------|
| CCRC12913    | (251)   | ------------------------------------------------------------ |
| CCRC14001    | (262)   | ------------------------------------------------------------ |
| GM-080       | (257)   | ------------------------------------------------------------ |
| CCRC16100    | (264)   | ------------------------------------------------------------ |
| KLB58        | (881)   | GAGTACGACCGCAAGGTTGAAACTCAAAGGAATTGACGGGGGCCCGCACAAGCGGTGGAG |
| PB4          | (539)   | ------------------------------------------------------------ |
| F31          | (883)   | GAGTACGACCGCAAGGTTGAAACTCAAAGGAATTGACGGGGGCCCGCACAAGCGGTGGAG |
| Consensus    | (901)   |                                                              |

|              |         | 961                                                         1020 |
|--------------|---------|------------------------------------------------------------------|
| CCRC12913    | (251)   | ------------------------------------------------------------ |
| CCRC14001    | (262)   | ------------------------------------------------------------ |
| GM-080       | (257)   | ------------------------------------------------------------ |
| CCRC16100    | (264)   | ------------------------------------------------------------ |
| KLB58        | (941)   | CATGTGGTTTAATTCGAAGCAACGCGAAGAACCTTACCAAGTCTTGACATCTTTTGATCA |
| PB4          | (539)   | ------------------------------------------------------------ |
| F31          | (943)   | CATGTGGTTTAATTCGAAGCAACGCGAAGAACCTTACCAAGTCTTGACATCTTTTGATCA |
| Consensus    | (961)   |                                                              |

|              |         | 1021                                                        1080 |
|--------------|---------|------------------------------------------------------------------|
| CCRC12913    | (251)   | ------------------------------------------------------------ |
| CCRC14001    | (262)   | ------------------------------------------------------------ |
| GM-080       | (257)   | ------------------------------------------------------------ |
| CCRC16100    | (264)   | ------------------------------------------------------------ |
| KLB58        | (1001)  | CCTGAGAGATCAGGTTTCCCCTTCGGGGGCAAAATGACAGGTGGTGCATGGTTGTCGTCA |
| PB4          | (539)   | ------------------------------------------------------------ |
| F31          | (1003)  | CCTGAGAGATCAGGTTTCCCCTTCGGGGGCAAAATGACAGGTGGTGCATGGTTGTCGTCA |
| Consensus    | (1021)  |                                                              |

FIG. 3 (continued)

```
                    1081                                                    1140
CCRC12913   (251)   ------------------------------------------------------------
CCRC14001   (262)   ------------------------------------------------------------
   GM-080   (257)   ------------------------------------------------------------
CCRC16100   (264)   ------------------------------------------------------------
    KLB58  (1061)   GCTCGTGTCGTGAGATGTTGGGTTAAGTCCCGCAACGAGCGCAACCCTTATGACTAGTTG
      PB4   (539)   ------------------------------------------------------------
      F31  (1063)   GCTCGTGTCGTGAGATGTTGGGTTAAGTCCCGCAACGAGCGCAACCCTTATGACTAGTTG
Consensus  (1081)

1141                                                    1200
CCRC12913   (251)   ------------------------------------------------------------
CCRC14001   (262)   ------------------------------------------------------------
   GM-080   (257)   ------------------------------------------------------------
CCRC16100   (264)   ------------------------------------------------------------
    KLB58  (1121)   CCAGCATTTAGTTGGGCACTCTAGTAAGACTGCCGGTGACAAACCGGAGGAAGGTGGGGA
      PB4   (539)   ------------------------------------------------------------
      F31  (1123)   CCAGCATTTAGTTGGGCACTCTAGTAAGACTGCCGGTGACAAACCGGAGGAAGGTGGGGA
Consensus  (1141)

1201                                                    1260
CCRC12913   (251)   ------------------------------------------------------------
CCRC14001   (262)   ------------------------------------------------------------
   GM-080   (257)   ------------------------------------------------------------
CCRC16100   (264)   ------------------------------------------------------------
    KLB58  (1181)   TGACGTCAAATCATCATGCCCCTTATGACCTGGGCTACACACGTGCTACAATGGATGGTA
      PB4   (539)   ------------------------------------------------------------
      F31  (1183)   TGACGTCAAATCATCATGCCCCTTATGACCTGGGCTACACACGTGCTACAATGGATGGTA
Consensus  (1201)

1261                                                    1320
CCRC12913   (251)   ------------------------------------------------------------
CCRC14001   (262)   ------------------------------------------------------------
   GM-080   (257)   ------------------------------------------------------------
CCRC16100   (264)   ------------------------------------------------------------
    KLB58  (1241)   CAACGAGTTGCGAGACCGCGAGGTCAAGCTAATCTCTTAAAGCCATTCTCAGTTCGGACT
      PB4   (539)   ------------------------------------------------------------
      F31  (1243)   CAACGAGTTGCGAGACCGCGAGGTCAAGCTAATCTCTTAAAGCCATTCTCAGTTCGGACT
Consensus  (1261)

1321                                                    1380
CCRC12913   (251)   ------------------------------------------------------------
CCRC14001   (262)   ------------------------------------------------------------
   GM-080   (257)   ------------------------------------------------------------
CCRC16100   (264)   ------------------------------------------------------------
    KLB58  (1301)   GTAGGCTGCAACTCGCCTACACGAAGTCGGAATCGCTAGTAATCGCGGATCAGCACGCCG
      PB4   (539)   ------------------------------------------------------------
      F31  (1303)   GTAGGCTGCAACTCGCCTACACGAAGTCGGAATCGCTAGTAATCGCGGATCAGCACGCCG
Consensus  (1321)

1381                                                    1440
CCRC12913   (251)   ------------------------------------------------------------
CCRC14001   (262)   ------------------------------------------------------------
   GM-080   (257)   ------------------------------------------------------------
CCRC16100   (264)   ------------------------------------------------------------
    KLB58  (1361)   CGGTGAATACGTTCCCGGGCCTTGTACACACCGCCCGTCACACCATGAGAGTTTGTAACA
      PB4   (539)   ------------------------------------------------------------
      F31  (1363)   CGGTGAATACGTTCCCGGGCCTTGTACACACCGCCCGTCACACCATGAGAGTTTGTAACA
Consensus  (1381)
```

FIG. 3 (continued)

```
                        1441                                                    1500
CCRC12913   (251)  ------------------------------------------------------------
CCRC14001   (262)  ------------------------------------------------------------
   GM-080   (257)  ------------------------------------------------------------
CCRC16100   (264)  ------------------------------------------------------------
    KLB58  (1421)  CCCGAAGCCGGTGGCGTAACCCTTTTAGGGAGCGAGCTGTCTAAGGTGGGACAAATGATT
      PB4   (539)  ------------------------------------------------------------
      F31  (1423)  CCCGAAGCCGGTGGCGTAACCCTTTTAGGGAGCGAGCTGTCTAAGGTGGGACAAATGATT
Consensus  (1441)

1501              1537
CCRC12913   (251)  -------------------------------
CCRC14001   (262)  -------------------------------
   GM-080   (257)  -------------------------------
CCRC16100   (264)  -------------------------------
    KLB58  (1481)  AGGGTGAAGTCGTAACAAGGTAGCTAAAGGAGA----
      PB4   (539)  -------------------------------
      F31  (1483)  AGGGTGAAGTCGTAACAAGG-AGCTGTAGGAGAACTA
Consensus  (1501)
```

FIG. 3 (continued)

SEQUENCE LISTING

<160> NUMBER OF SEQ ID NOS: 2

<210> SEQ ID NO 1
<211> LENGTH: 18
<212> TYPE: DNA
<213> ORGANISM: Artificial
<220> FEATURE:
<223> OTHER INFORMATION: L. paracasei specific 16S rRNA

<400> SEQUENCE: 1
caccgagatt caacatgg					18

<210> SEQ ID NO 2
<211> LENGTH: 24
<212> TYPE: DNA
<213> ORGANISM: Artificial
<220> FEATURE:
<223> OTHER INFORMATION: conserved 16S rRNA

<400> SEQUENCE: 2
cccactgctg cctcccgtag gagt				24

LACTOBACILLUS PARACASEI STRAIN GM-080 FOR TREATING ALLERGY RELATED DISEASES

BACKGROUND OF THE INVENTION

1. Field of the Invention

The invention mainly relates to a novel microorganism strain *Lactobacillus paracasei* GM-080 and its use for stimulating IFN-γ secretion and treating allergy related diseases.

2. Description of the Related Art

Allergy refers to an acquired potential to develop immunologically mediated adverse reaction to normally innocuous substances. Allergic reaction provokes symptoms such as itching, coughing, wheezing, sneezing, watery eyes, inflammation and fatigue. It is normally believed that allergic reaction includes an early specific immune response and a late inflammatory reaction. It is reported that allergens (e.g., pollens and mite dust) mediate the early phase of allergy by stimulating high affinity immunoglobulin (IgE) receptors. For instance, mast cells and basophils, when stimulated by allergens, will release histamine and cytokines. The cytokines released from mast cells and basophils then mediate the late phase of allergy by recruiting inflammatory cells. It is also reported that the influx of eosinophils, macrophages, lymphocytes, neutrophils and platelets starts the vicious inflammatory cycle. This late phase of allergy amplifies the initial immune response, which in turn triggers the release of more inflammatory cells (Blease et al. Chemokines and their role in airway hyper-reactivity. Respir Res 2000; 1:54–61).

Various therapies have been pursued in order to treat the symptoms of allergies. Among them, anti-allergics and histamine H-receptor antagonists (anti-histamines) have been used. Histamine antagonists are administered to antagonize the action of histamine released from mast cells in response to the presence of allergens. They reduce the redness, itching and swelling caused by the action of histamine on the target tissues, and serve to prevent or alleviate many of the symptoms resulting from degranulation of mast cells. However, anti-histamines have also been associated with adverse reactions such as diminished alertness, slowed reaction times and somnolence (U.S. Patent No. 6,225,332).

There are also some reports on the treatment of allergies by regulating cytokines. Among them, interferon-γ (IFN-γ) was found to inhibit the over-expression of cytokines in Th2 lymphocytes, especially the secretion of IL-4 to lower the proliferation of B cells. Also, IFN-γ could stimulate the immune response of Th1 and repress the synthesis of IgE (Sareneva T et al. Influenza A virus-induced IFN-α/β and IL-18 synergistically enhance IFN-γ gene expression in human T cells. *J Immunol* 1998; 160:6032–6038; Shida K et al. *Lactobacillus casei* inhibits antigen-induced IgE secretion through regulation of cytokine production in murine splenocyte cultures. *Int Arch Allergy Immunol* 1998; 115:278–287). Since IFN-γ can repress B cell proliferation and IgE secretion, it is believed that IFN-γ is effective in treating allergy.

Lactic acid bacteria, which are gram-positive bacteria, are commonly used in industrial food fermentations. In recent studies, lactic acid bacteria were shown to stimulate IFN-γ secretion of cells (Contractor NV et al. Lymphoid hyperplasia, autoimmunity and compromised intestinal intraepithelial lymphocyte development in colitis-free gnotobiotic IL-2-deficient mice. *J Immunol* 1998; 160:385–394). Some specific lactic acid bacteria, such as *Bifidobacterium lactis* and *Lactobacillus brevis* subsp., were found to stimulate IFN-γ secretion of lymphocytes in blood derived from mice and humans (U.S. Patent Publication No. U.S. 2002/0031503 A1; U.S. Patent. No. 5,556,785). It was also reported that lactic acid bacteria could stimulate lymphocytes derived from humans or mice to secrete Interleukin-12 (IL-12), which was a T cell stimulatory cytokine activating T cells and NK cells to secrete IFN-γ (Hessle et al. *Lactobacilli* from human gastrointestinal mucosa are strong stimulators of IL-12 production. *Clin Exp Immunol* 1999; 116:276–282).

*Lactobacillus paracasei* has been used for manufacturing Cheddar and Italian ewe cheeses for a long time. It was found to grow and sustain high viability in cheese during ripening (Gardiner, G., Ross, R. P., Collins, J. K., Fitzgerald, G., Stanton, C. Development of a probiotic cheddar cheese containing human-derived *Lactobacillus paracasei* strains. *Appl Environ Microbiol.* 1998; 64: 2192–2199; Angelis, M., Corsetti, A., Tosti, N., Rossi, J., Corbo, M. R., Gobbetti, M. Characterization of non-starter lactic acid bacteria from Italian ewe cheeses based on phenotypic, genotypic, and cell wall protein analyses. *Appl Environ Microbiol.* 2001; 67: 2011–2020). *L. paracasei* was noticed to produce antibacteria and anti-yeast compounds such as $H_2O_2$ and proteinaceous active substance in human vagina and oral cavity (Atanassova, M., Choiset, Y., Dalgalarrondo, M., Chobert, J.-M., Dousset, X., Ivanova, I., Haertké, T. Isolation and partial biochemical characterization of a proteinaceous antibacteria and anti-yeast compound produced by *Lactobacillus paracasei* subsp. *paracasei* strain M3. *Int. J. Food Microibiol.* 2003; 87: 63–73; Ocaña, V. S., Holgado, A. A. P. de R., Nader-Macias, M. E. Growth inhibition of *Staphylococcus aureus* by $H_2O_2$-producing *Lactobacillus paracasei* subsp. *paracasei* isolated from the human vagina. *FEMS Immunol. Med. Microbiol.* 1999; 23: 87–92; Sookkhee S., Chulasiri, M., Prachyabrued, W. Lactic acid bacterial form healthy oral cavity of Thai volunteers: inhibition of oral pathogens. *Journal of Applied Microbiology* 2001; 90:172–179).

SUMMARY OF THE INVENTION

The invention provides a novel microorganism strain *Lactobacillus paracasei* GM-080.

In another aspect, the invention provides a composition comprising the microorganism strain *Lactobacillus paracasei* GM-080.

In another aspect, the invention provides a method for treating allergy related diseases in a subject comprising administering said subject with a composition comprising the microorganism strain *Lactobacillus paracasei* GM-080; wherein the complication is preferably selected from the group consisting of airway hyperreactivity and inflammation, atopic dermatitis, allergic conjunctivitis, rhinitis, sinusitis, hypersensitive pneumonia, extrinsic allergic alveolitis, urticaria, eczema, anaphylaxis, angioedema, allergic and migraine headache, certain gastrointestinal disorders, and asthma.

In still another aspect, the invention provides a method for stimulating IFN-T secretion in a subject comprising administering said subject with a composition comprising the microorganism strain *Lactobacillus paracasei* GM-080.

BRIEF DESCRIPTION OF THE DRAWINGS

FIG. 3 illustrates the 16s rDNA sequence alignment of GM-080 and lactic acid bacterial strains CCRC12913, CCRC14001, CCRC16100, KLB58, PB4, and F31.

DETAILED DESCRIPTION OF THE INVENTION

Figure 1:
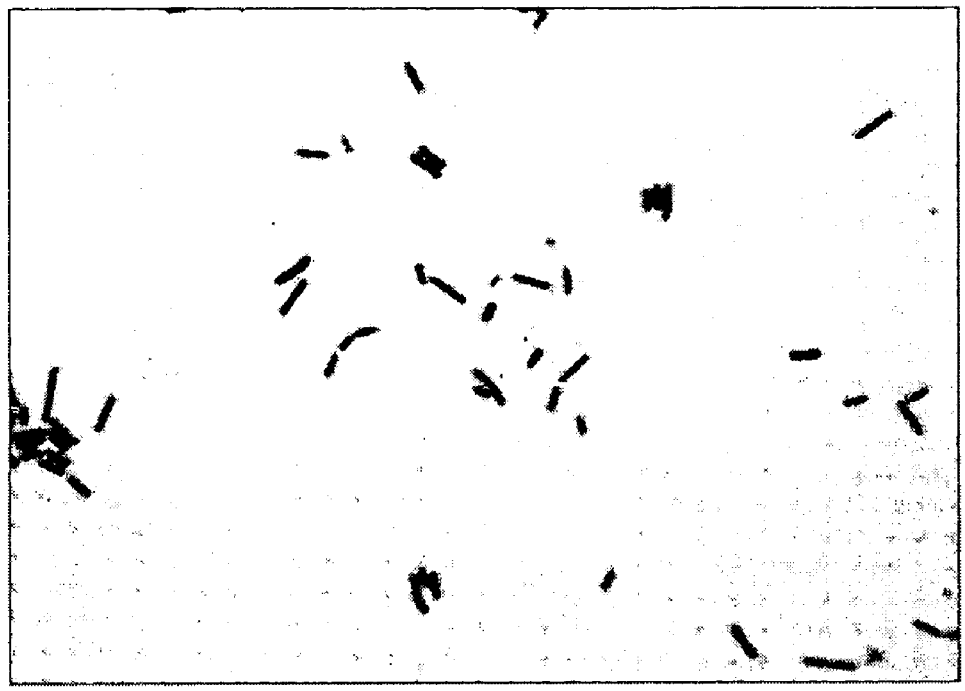
FIG. 1 illustrates the 1000×microscopic view of GM-080 subjected to Gram stain.

The invention provides a novel microorganism strain *Lactobacillus paracasei* GM-080, which is capable of treating allergy. The strain GM-080 was deposited with the China Center for Type Culture Collection (CCTCC), Wuhan University, Wuhan 430072, People's Republic of China under the accession number of CCTCC M 204012 on Feb. 19, 2004.

The *Lactobacillus paracasei* GM-080 is isolated from the healthy human GI tract. A tissue sample taken from the stomach, intestine or duodenum is suspended in a MRS broth medium containing 100 μg/mL ampicillin cultured at 37° C. for 2 days and then streak plating on agar plates. The lactic acid bacterial colonies growing on the plates can be preliminarily screened under a microscopy examination. Candidate strains are then co-cultured with splenocytes. The amount of IFN-γ thus produced by splenocytes in the broth is determined. Then, GM-080 is selected for its high productivities of IFN-γ.

The mycological characteristics of the GM-080 are shown below:

(a) Morphological Characteristics:
(1) Shape and size of cell: *bacillus*, which has a rod-like shape with round edge when the cells after cultured at 37° C. overnight in MRS broth were observed with a microscope.
(2) Motility: motile
(3) Flagella: none
(4) Sporulation: no spore-forming
(5) Gram-stain: positive (b) Cultural Characteristics:
(1) Medium: MRS broth (DIFCO®0881), final pH 6.5±0.2
(2) Cultural condition: 37° C. anaerobic or aerobic culture
(3) Antibiotic resistance: Ampicillin 100 μg/mL (c) Physiological Characteristics:
(1) Catalase: positive
(2) Oxidase: negative
(3) API 50 CHL test: API 50 CHL system is used for identification of lactic acid bacteria. By assaying the responses of a serious of enzymes, the characters of the lactic acid are established. The result of API 50 CHL test of GM-080 is listed in Table 1:

TABLE 1

Reference: GM-080
VERY GOOD IDENTIFICATION TO THE GENUS
Strip: API 50CHL
Profile: -----+---- +++++---++ --+-++++++ -++------+ +-+----+--
0 - GLY - ERY - DARA - LARA - RIB + DXYL - LXYL - ADO - MDX - GAL +
GLU + FRU + MNE + SBE + RHA - DUL - INO - MAN + SOR + MDM - MDG -
NAG + AMY - ARB + ESC + SAL + CEL + MAL + LAC + MEL - SAC + TRE +
INU - MLZ - RAF - AMD - GLYG - XLT - GEN + TUR + LYX - TAG + DFUC -
LFUC - DARL - LARL - GNT + 2 KG - 5 KG -

| Significant taxa | % Id. | T | Tests against | |
| --- | --- | --- | --- | --- |
| Lacto.para.paracasei | 1 | 94.9 | 0.74 | 2 |
| Lacto.para.paracasei Next choice | 3 | 5.0 | 0.59 | 5 |
| Lacto.rhamnosus | | 0.1 | 0.39 | 4 |

TABLE 1-continued

| | | | | | |
|---|---|---|---|---|---|
| Lacto.para.paracasei | 1:2 test(s) against | | | | |
| AMYGDALINE | (AMY) | 98% | MELEZITOSE | (MLZ) | 93% |
| Lacto.para.paracasei | 3:5 test(s) against | | | | |
| L-SORBOSE | (SBE) | 20% | D-SORBITOL | (SOR) | 20% |
| AMYGDALINE | (AMY) | 99% | D-TURANOSE | (TUR) | 20% |
| GLUCONATE | (GNT) | 20% | | | |
| Next choice | | | | | |
| Lacto.rhamnosus | :4 test(s) against | | | | |
| L-RHAMNOSE | (RHA) | 100% | METHYL-D-CLUCOSIDE | (MDG) | 85% |
| AMYGDALINE | (AMY) | 99% | MELEZITOSE | (MLZ) | 99% |

Figure 2:
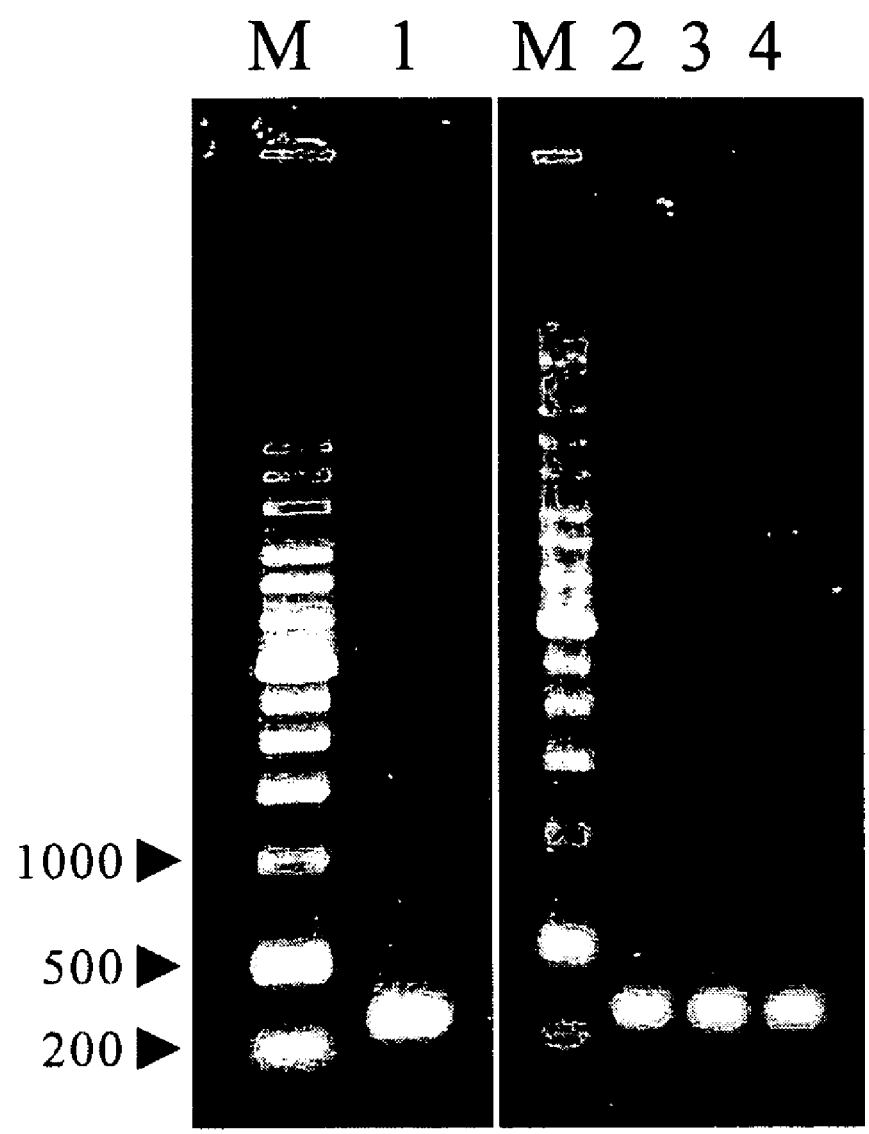
FIG. 2 illustrates the results of agarose gel analysis of 16s rDNA fragments amplified by PCR of GM-080 and lactic acid bacterial strains CCRC12913, CCRC14001 and CCRC16100; M represents molecular marker; 1 represents GM-080; 2 represents CCRC12913; 3 represents CCRC 14001; and 4 represents CCRC 16100.

(d) Genetic Characteristics:

16S rDNA sequence analysis of GM-080 is determined. The result shows that GM-080 is highly homologous to other *Lactobacillus paracasei* strains (as shown in FIG. 2). Moreover, the phylogenetic distance tree is shown in FIG. 3. Also, randomly amplified polymorphic DNA (RAPD analysis) was performed. It shows that GM-080 belongs to *Lactobacillus paracasei*, but has a specific 16S rDNA sequence. Given the above, GM-080 is a novel *Lactobacillus paracasei* strain.

Figure 4:
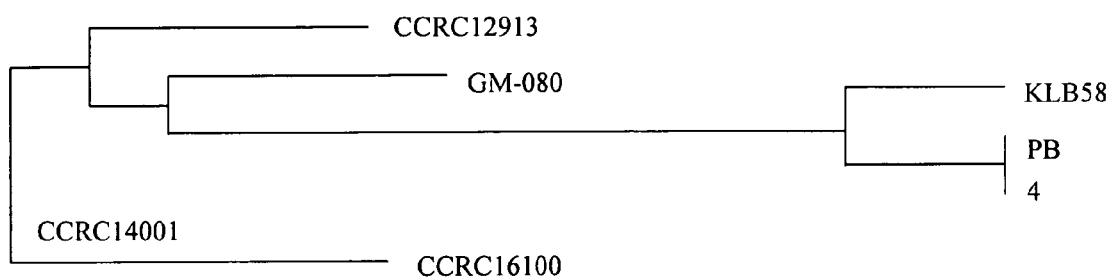
FIG. 4 illustrates a 16s rDNA phylogenetic distance tree comparing GM-080 of the invention with related lactic acid bacteria.

(e) Cell wall proteins of GM-080:

The cell wall proteins of GM-080 show similar pattern when compared with other conventional *Lactobacillus paracasei* strains. The SDS-PAGE patterns of the cell wall proteins of GM-080 are shown in FIG. 4.

(f) Standardized detection system for identifying GM-080:

The standard detection system for identifying microorganism is disclosed in U.S. patent application Ser. No. 10/446,781, filed on May 29, 2003, using gene expression difference of a test cell line culturing with and without a given microorganism as a marker for identification. The genes tested are listed in Table 2.

TABLE 2

| Gene | Gene | Gene | Gene |
|---|---|---|---|
| FHR-4 | FGF19 | FKBP1B-a | FGF20 |
| FGF13-c | FGF10 | FGF14 | FGF11 |
| FGF5-b | FGF1-a | FGF6 | FGF1-b |
| FCGBP | FCAR-f | FCGR1A | FCAR-g |
| FADD | ELK3 | FCAR-a | ENG |
| ELA2 | CXCR4 | EGR1 | CXCL16 |
| CX3CR1 | CSF2RB | CXCL1 | CSF3R-a |
| CRL3 | COL3A1 | CRTAM | CR1 |
| CMRF-35H | CHUK | CNR1-a | CKTSF1B1 |
| CDC25A | CD163 | CDH3 | CD164 |
| CD97-b | CD81 | CD109 | CD83 |
| CD79A-a | CD58 | CD79A-b | CD59 |
| CD37 | CD22 | CD38 | CD24 |
| CD7 | CD3G | CD8A | CD3Z |
| CD2-a | CCRL2 | CD2-b | CD1A |
| CCR4 | CCL25 | CCR5 | CCL26 |
| CCL19 | CCL8 | CCL20 | CCL11 |
| CAMK4 | C9 | CCBP2 | CABIN1 |
| C5 | C1S | C6 | C2 |
| C1QTNF2 | BTNL2 | C1QTNF3 | BY55 |
| BLR1-b | BCL2-a | BLR1-c | BCL2-b |
| AP1S1-b | ALDH1A1 | AP1S1-c | AOAH |
| ADRB2 | ACVR1B-c | ATF2-a | ACVR1B-d |
| FKBP1B-b | FGF21 | FLJ14639 | FGF22 |
| FGF16 | FGF12-a | FGF17 | FGF12-b |
| FGF7 | FGF2 | FGF8-a | FGF3 |
| FCGR2A | FCAR-h | FCGR2B | FCER1A |
| FCAR-b | EP300 | FCAR-c | EPO |
| EGR2 | CXCR3 | EGR3 | CYSLTR1 |
| CXCL10 | CSF3R-b | CXCL13 | CTLA1 |
| CSNK2A1 | CR2 | CSNK2B | CREB1-a |

TABLE 2-continued

| Gene | Gene | Gene | Gene |
|---|---|---|---|
| CNR1-b | CIAS1 | CPA3 | CIS4 |
| CDKN1A | CD200R | CDKN2B-a | CD209 |
| CD151-a | CD84 | CD151-b | CD84-H1 |
| CD79B-a | CD63 | CD79B-b | CD68 |
| CD44 | CD33 | CD47 | CD34-a |
| CD8B1 | CD4 | CD9 | CD5 |
| CD2AP | CD1B | CD2BP2 | CD1C |
| CCR6 | CCL27 | CCR8 | CCL28 |
| CCL21 | CCL13 | CCL23-a | CCL16 |
| CCL1 | CALM1 | CCL2 | CALM2 |
| C7 | C3 | C8A | C3AR1 |
| C1QTNF4 | C1QA | C1QTNF6 | C1QB |
| BMPR1A | BCL2-c | BMPR1B | BCL3 |
| AP1S2 | AMH | ATF2-b | AMHR2 |
| AGT | ACVR2 | AIF1-a | ACVR2B |
| ACHE-b | ACE-a | ACVR1 | ACE-b |
| FOG2 | FGF23 | FOS | FHOD2 |
| FGF18-a | FGF13-a | FGF18-b | FGF13-b |
| FGF8-b | FGF4 | FGF9 | FGF5-a |
| FCGR3A | FCER1G | FCGRT | FCER2 |
| FCAR-d | ETEA | FCAR-e | EPX |
| EGR4 | DAF | ELK1 | E48 |
| CXCL5 | CTLA4 | CXCL6 | CTRP5 |
| CSF1R | CREB1-b | CSF2RA | CREBBP |
| COL1A1 | CMA1 | COL1A2 | CMRF35 |
| CDKN2B-b | CD209L | CER1 | CD244 |
| CD151-c | CD86-a | CD151-d | CD97-a |
| CD79B-c | CD72 | CD80-a | CD74 |
| CD48 | CD34-b | CD53 | CD36 |
| CD14 | CD5L | CD19 | CD6 |
| CD3D | CD1D | CD3E | CD1E |
| CCR9-a | CCR1 | CCR9-b | CCR3 |
| CCL23-b | CCL17 | CCL24 | CCL18 |
| CCL5 | CALM3 | CCL7 | CAMK2B |
| C8B | C4BPA | C8G | C4BPB |
| C1QTNF7 | C1QBP | C1R | C1QR1 |
| BMPR2-a | BF | BMPR2-b | BLR1-a |
| BAD-a | ANXA3 | BAD-b | AP1S1-a |
| AIF1-b | ACVRL1 | ALDH1A2 | ADRB1 |
| ACVR1B-a | ACE2 | ACVR1B-b | ACHE-a |
| NCAM2 | MUC4-c | NCF2 | MYC |
| MORF | MIF | MUC1 | MMD |
| MEF2B | MAPK14-a | MEF2D | MAPK14-b |
| MAPK8 | MAP3K14 | MAPK9 | MAP3K7-a |
| MAF | MADH3 | MAP2K7-a | MADH4 |
| LY6H | LY6E | LY75 | LY6G5B |
| LTB-b | LLT1 | LTBR | LTB4R-a |
| LOC163702 | LOC139429 | LOC201595 | LOC145314 |
| LILRB5 | LILRA2 | LOC122687 | LILRA3 |
| KPNA5 | JAK3 | KPNB3 | JUN |
| ITGB1-a | ITGA10 | ITGB1-b | ITGA11 |
| ITGA3-b | IRF6 | ITGA4 | IRF7 |
| IRAK3 | ILF2 | IRAK4 | ILF3-a |
| IL19 | IL-17RE-b | IL20 | IL-17RE-c |
| IL-17RC-b | IL16 | IL-17RC-c | IL17 |
| IL11 | IL3RA | IL11RA-a | IL411 |
| IRAK2-a | IGSF6 | IL1F8 | IGSF8 |
| IGFBP3 | IFNW1 | IGLL1 | IFRD1 |
| IFNA4 | IFIT2 | IFNA8 | IFIT4 |
| IFI16 | ICOS | IFI27 | ICAM3 |

TABLE 2-continued

| Gene | Gene | Gene | Gene |
|---|---|---|---|
| HCGIX | GPR84 | HF1 | GRLF1 |
| GDF10 | FOSL1 | GBP2 | FOSL2 |
| NFAT5-b | ITGB3 | NFAT5-c | ITGB3BP |
| NCF4-a | MYD88 | NCF4-b | MYF5 |
| MUC2 | MME-a | MUC3B | MME-b |
| MHCBFB | MCP-a | MHC2TA | MCP-b |
| MAPK10-a | MAP3K7-a | MAPK10-b | MAP3K7-c |
| MAP2K7-b | MADH5 | MAP3K1 | MADH6 |
| LY9 | LY6G5C | LYL1 | LY6G6C |
| LTB4R-b | LTB4R2-a | LTB4R2-b | LAG3-b |
| LOC205360 | LOC145355 | LOC221937 | LOC145497 |
| LOC128342 | LILRB1 | L0C136520 | LILRB2 |
| LAG3-a | JUNB | LAT | JUND |
| ITGBL1 | ITGB4 | ITK | ITGB4BP |
| ITGB1-c | ITGAE | ITGB1-d | ITGAL |
| ITGA5 | IRTA1 | ITGA6 | IRTA2 |
| IRF2 | ILF3-b | IRF3 | ILF3-c |
| IL21 | IL21R | IL-17RE-e |
| IL-17RC-d | IL17C | IL-17RC-e | IL17F |
| IL11RA-b | IL7 | IL11RA-c | IL8 |
| IL1F7 | IGSF9 | IL2RA | IKBKB |
| IGSF1 | IFRD2 | IGSF2 | IGBP1 |
| IFNAR1 | IFITM1 | IFNAR2 | IFNA14 |
| IFI30 | ICAM4-a | IFI35 | ICAM4-b |
| HM74 | GSCL | HOXA1-a | GSK3A |
| GFI1 | FST | GPR2 | FY |
| NFAT5-d | ITGB7-a | NFATC1 | ITGB8 |
| NCF4-c | NBL1 | NFAT5-a | NCAM1 |
| MUC4-a | MMEL2 | MUC4-b | MMP9 |
| MICA | MCP-c | MICB | MEF2A |
| MAPK10-c | MAP3K7-b | MAPK10-d | MAPK3 |
| MAP3K2 | MADH7 | MAP3K7IP1 | MADH9 |
| MADH1 | LY6G6D | MADH2 | LY6G6E |
| LY117 | LTA | LY64 | LTB-a |
| LOC221938 | LOC147137 | LEP-b | LOC149620 |
| LOC136531 | LILRB3 | LOC136535 | LILRB4 |
| LEP-a | KITLG-a | LILRA1 | KITLG-b |
| IVL | ITGB5 | JAK2 | ITGB6 |
| ITGB2 | ITGAM | ITGB1BP2 | ITGAV |
| ITGA7 | ITGA2 | ITGA8 | ITGA3-a |
| IRF5-a | IRAK1 | IRF5-b | IRAK2-b |
| IL22R | IL18BP | IL-23R | IL18R1 |
| IL-17RC-f | IL17R | IL-17RE-a | IL-17RC-a |
| IL14 | IL8RA | IL15RA | IL8RB |
| IL2RB | IKBKG | IL2RG | IKKE |
| IGSF3 | IGHMBP2 | IGSF4 | IGF1 |
| IFNGR1 | IFNA2 | IFNGR2 | IFNA21 |
| IFI44 | ICAM5 | IFIT1 | IF |
| HOXA1-b | GSK3B | HRAS | HCC-4 |
| GPR31 | GATA1 | GPR44 | GATA6 |
| IL5 | IL1R1 | IFNA1 | IL6ST |
| IL10RB | IL10RA | ICAM1 | IL13RA2 |
| GATA3 | IL1B | IL10 | IL2 |
| MIP-A | LOC126133 | Uricase | HNF4A |
| LOC161823 | PGK1 | G6PT1 | NT5C1A |
| DHFR | PPARG-b | PGK2 | LOC200895 |
| LOC132198 | XDH | PPARG-a | GDA |
| TCF2-a | SLC22A12-a | TCF2-b | SLC22A12-b |
| ALDH2 | PRPSAP2 | MTHFR | VLDLR |
| LOC205855 | YY1 | NP | PPAT |
| VAV3 | TRPV6-c | VEGF | TSA1902 |
| TRAF4-a | TRAF1 | TRAF4-b | TRAF2-a |
| TNFRSF7 | TNFSF5 | TNFRSF8-a | TNFSF6 |
| TLR10 | TLR6 | TNFAIP3 | TLR7 |
| TLR3 | TGIF-b | TLR4-a | TGIF-c |
| TGFB2 | TBX21 | TGFB3 | TCF8 |
| STAT2 | SOCS5-a | STAT3 | SOCS5-b |
| SERPING1 | SEMA4B | SFN | SEMA4C |
| SE20-4 | RPL13A | SEMA3A | RUNX1 |
| REL | PRL | RELA | PTGER2 |
| PLAU | PECAM1 | PPP3CB | PFC |
| P2RX7 | NOS2A-b | PAK1 | NPPB |
| NFKBIB | NFATC2 | NFKBIE | NFATC3 |
| IL5RA | IL1R2 | None | IL9-a |
| STAT1-c | STAT1-b | ITGB7-b | CCR2-c |
| IL13RA1 | CCR2-a | IL18 | CD69 |
| TGFB1 | IL27 | CD28 | IL1A |

TABLE 2-continued

| Gene | Gene | Gene | Gene |
|---|---|---|---|
| VCAM1-b | JAK1 | TNF-b | CSF3 |
| IL6R | STAT1-a | IL12RB2 | IL15 |
| 15MD2 | HNF-1B | GBP1 | 15MD-1 |
| LOC169330 | S100A8 | IMPDH1 | S100A9 |
| MTHFD2 | HDLBP | G6PC | LRP8 |
| PRPS2 | HPRT1 | PRPSAP1 | APRT |
| XCL1 | TSC22 | XCR1 | TYK2 |
| TRAF5 | TRAF2-b | TRAF6 | TRAF2-c |
| TNFRSF8-b | TNFRSF11A | TNFRSF9 | TNFRSF1A |
| TNFSF11-a | TLR8-a | TNFSF11-b | TLR8-b |
| TLR4-b | TH1L | TLR4-c | TIMP1 |
| TGFBR1 | TCP10 | TGFBR2 | TDGF1 |
| STAT4 | SOCS4 | STATI2 | SSI-1 |
| SIVA-a | SEMA4D | SIVA-b | SEMA4F |
| SEMA3B | RUNX2 | SEMA3C | SCYA3 |
| RELB | PTPRC-a | RIPK1 | PTPRC-b |
| PPP3CC | PIGR | PPP3R1 | PILR(ALPHA) |
| PDE4B | NUP214-a | PDGFB-a | NUP214-b |
| NFKBIL1 | NFATC4 | NFKBIL2 | NFKB1 |
| CSF1 | IL9-b | CD80-b | IL13 |
| CCR2-b | CD86 | IL4 | IFNB1 |
| CEBPB | TIM3 | IRF1 | IL4R |
| TP53 | IL12B | TNF-a | SERPINA3 |
| VCAM1-a | SCYA4 | CCR7 | IL12A |
| IL12RB1 | CSF2 | ADSS | STAT6 |
| IMPDH2 | IL6 | LGALS9 | IFNG |
| UMOD | PTGS2 | LOC223071 | TCF2-c |
| PRPS1 | APOE | ZNF144 | APOB |
| XPO5 | ADA | TRPV6-b | DPP4 |
| TRPV6-a | VAV1 | TPSD1 | VAV2 |
| RSF21 | TRAF3-a | TNFSF4 | TRAF3-b |
| TNFSF11-c | TNFRSF1B | TLR5 | TNFRSF21 |
| TLR4-d | TLR9-a | TGIF-a | TLR9-b |
| TGFBR3 | TLR1 | TBXA2R | TLR2 |
| TACTILE | TFCP2 | SLAM | TGFA |
| SLA | SSI-3 | SEMA3F | SUDD |
| SEMA3E | SEMA4G | RNASE3 | SEMA7A |
| RNASE2 | SCYE1 | PRG2 | SDF2 |
| PRKG1 | PTPRC-c | PDPK1 | RDC1 |
| PDGFB-b | PILR(BETA) | NOS2A-a | PIN1 |
| NMA | OPRD1 | negative | ORM1 |
| ACTB | NFKB2 | G6PD | NFKBIA |

The standard detection system for identifying GM-080 takes Jurkat cell line as a test cell line. When comparing the expression patterns of culturing Jurkat cell line with and without GM-080, the genes listed in Table 3 are significantly different. Furthermore, the detection results of other *Lactobacillus paracasei* strains, CCRC 12193 and CCRC 12188, are also shown in Table 3. It indicated that these strains are all *Lactobacillus paracasei*, but belong to different strains.

TABLE 3

| Gene name | Paracasei CCRC12193 | GM-080 | Paracasei CCRC12188 |
|---|---|---|---|
| ADA | ++++++ | ++++ | ++ |
| BAD-a | ++ | +++ | + |
| BCL3 | + | + | − |
| BLR1-c | — | + | − |
| BMPR2-a | ++ | ++ | + |
| CCL2 | − | + | − |
| CD2AP | ++ | ++ | + |
| CD2-b | ++ | ++ | + |
| CD38 | ++ | ++ | − |
| CD3G | ++++++ | ++++++ | ++++++ |
| CD48 | ++ | ++ | + |
| COL1A2 | — | − | — |
| CR2 | ++ | ++ | + |
| CREB1-a | ++ | ++ | + |
| CREB1-b | +++ | +++ | + |
| CX3CR1 | ++ | +++ | ++ |

TABLE 3-continued

| Gene name | Paracasei CCRC12193 | GM-080 | Paracasei CCRC12188 |
|---|---|---|---|
| DAF | ++ | +++ | + |
| ETEA | ++ | ++ | + |
| FCAR-h | +++ | +++++ | ++ |
| FGF23 | + | ++ | + |
| FHOD2 | ++ | ++ | + |
| HOXA1-a | + | ++ | + |
| IFNAR1 | ++++ | +++++ | ++ |
| IFNGR1 | ++ | +++ | + |
| IKKE | ++ | ++ | − |
| IL14 | + | ++ | + |
| IL17R | ++++ | ++ | + |
| IL4R | +++ | +++ | + |
| IL7 | ++ | ++ | + |
| JAK1 | ++ | ++ | + |
| LEP-a | + | +++ | + |
| LOC200895 | + | ++ | + |
| LY117 | ++ | +++ | − |
| MADH4 | ++ | ++ | + |
| MADH5 | +++ | +++ | + |
| MAP3K14 | ++ | ++ | + |
| MAPK14-a | ++ | ++ | + |
| MAPK3 | ++ | +++ | + |
| MCP-a | +++ | +++ | + |
| MCP-c | ++ | ++ | + |
| PDPK1 | ++ | ++ | + |
| REL | ++ | ++ | + |
| RIPK1 | ++ | ++ | + |
| SEMA3C | − | ++ | + |
| TGFBR2 | ++ | ++ | − |
| TLR3 | +++ | +++ | + |
| TNFSF4 | +++ | +++ | + |
| TRAF3-a | +++ | ++ | ++ |
| TRAF6 | + | ++ | + |
| TSC22 | +++ | ++ | + |

+: the gene expression increases in 2 folds
−: the gene expression decrease in 2 folds GM-080 is active after treating HCl solution (pH 2.0) for 3 hours and then gall for 4 hours. Therefore, GM-080 is regarded as remaining active in digestion. GM-080 is isolated from a healthy subject and is safe, natural, nontoxic, and meet the G.R.A.S. (Generally Regarded as Safe) standard.

Furthermore, GM-080 strongly adhered to the epithelial cells in the intestine. Given the above, GM-080 can stay in the intestine for a longer time to act for modulating physiological functions. Also, by occupying the adhesion sites of the epithelial cells in the intestine, GM-080 bars other pathogenic bacteria from adhering to the intestine. GM-080 is regarded as a good probiotic bacterium.

According to the invention, GM-080 is found to stimulate IFN-γ secretion, and can be used for treating allergy related disease.

In one aspect, the invention provides a composition comprising GM-080. More preferably, the composition comprising GM-080 is used for stimulating IFN-γ secretion, which is useful for treating allergy related diseases.

As used herein, the term "allergy related diseases" refers to the diseases wherein a systematic reaction to a normal innocuous environmental antigen, which results from the interaction between the antigen and antibody or T cells produced by earlier exposure to the same antigen. The term "allergic reaction" as used herein refers to a response to innocucous environmental antigens or allergens due to pre-existing antibody or T cells. There are various immune mechanisms of allergic reactions, but the most common type is the binding of allergen to IgE antibody on mast cells that causes asthma, hay fever, and other common allergic reactions. The allergy related diseases include airway hyperreactivity and inflammation, atopic dermatitis, allergic conjunctivitis, rhinitis, sinusitis, hypersensitive pneumonia, extrinsic allergic alveolitis, urticaria, eczema, anaphylaxis, angioedema, allergic and migraine headache, certain gastrointestinal disorders, and asthma. According to a preferred embodiment of the invention, the allergy related disease is airway hyperreactivity or inflammation. In another aspect, the allergy related disease is associated with exposure to airborne allergen (aeroallergen) such as pollens, molds, animal dander, and insects.

As used herein, the term "aeroallergen" is defined as having at least the following characteristics: specific antigenic groupings that evoke active reaginic responses, and ambient exposure levels to which can lead to overt tissue changes in sensitive subjects. Aeroallergens are airborne particles that can cause respiratory, cutaneous, or conjunctival allergy. The water-soluble portion of ragweed pollen, for example affects the respiratory and conjunctival mucosa, and the lipid-soluble allergens of ragweed pollen can cause a typical contact dermatitis on exposed skin.

GM-080 is selected to have the ability to stimulate IFN-γ secretion when co-incubated with splenocytes and peripheral blood mononuclear cells (PBMCs) in vitro. Furthermore, in the model according to the invention, animals sensitized with an aeroallergen and then treated with GM-080 are observed to increase IFN-γ secretion. Furthermore, the amount of aeroallergen specific IgE is significantly lowered after treatment. On the other hand, the amount of allergen specific IgG does not show significant difference between before and after treatments. In addition, the eosinophil cell count in the bronchoalveolar lavage fluids (BALF) is enormously decreased; however, the macrophage and lymphocyte counts in BALF are enormously increased. It evidenced that the inflammation was relieved.

According to the invention, GM-080 for use in the treatment of allergy can be live or inactive. Preferably, GM-080 is inactive. For instance, the live bacterial strains can be treated with a heating step or other treatments commonly used in the art for killing the lactic acid bacterial as the inactive strains.

According to the invention, the lactic acid bacterial strain can be included in a pharmaceutical composition, dietary supplement, food, health food, medical food, or the components thereof, which are normally administered by people. In a preferred embodiment of the invention, the lactic acid bacterial strain can be delivered in food form, such as in a coagulated milk product that prepared through the fermentation of lactic acid in milk. The food products prepared according to the invention can be conveniently administered to infants or children.

In another aspect, the invention provides a method for treating allergy related disease in a subject comprising administering said subject with a composition comprising the isolated microorganism GM-080.

In still another aspect, the invention provides a method for stimulating IFN-γ secretion in a subject comprising administering said subject with a composition comprising the isolated microorganism GM-080.

The following Examples are given for the purpose of illustration only and are not intended to limit the scope of the present invention.

EXAMPLE 1

Isolation of *Lactobacillus paracasei* GM-080

Sample: A piece of human stomach, intestine or duodenum tissue taken by an endoscope was cultured in 2 mL of *Lactobacillus* MRS Broth (DIFCO® 0881) containing 100 µg/mL of ampicillin for about two days at 37° C. The broth was plated on MRS agar containing $CaCO_3$ and incubated at 37° C. for two days. Single colony growing on the plate was selected and subjected to Gram-stain. Gram-positive bacteria were then selected. All of the strains were cultured in *Lactobacillus* MRS broth at 37° C. to the stationary phase, and collected by centrifuging at 3000 g for 15 minutes and washed with 2 mL and 1 mL PBS (phosphate buffered saline, pH 7.2). The cultures of the strains were re-suspended in 1 mL PBS and then heated at 95° C. for 30 minutes, and were then autoclaved and stored in PBS at −20° C.

Isolation of splenocytes: Five mL blood samples derived from healthy volunteers were added with 5 mL Ficoll-Hypaque (17-1400-02, Pharmacia) and then centrifuged at 500 g for 30 minutes. The splenocytes were taken. In each splenocyte sample, the cell density was adjusted to $5 \times 10^6$ cells per sample. The splenocyte samples were incubated in 2 mL RPMI 1640 (pH 7.7) for 6 hours.

Isolation of peripheral blood mononuclear cells: Five mL blood samples derived from healthy volunteers were added with 5 mL Ficoll-Hypaque (17-1400-02, Pharmacia) and then centrifuged at 500 g for 30 minutes. The peripheral blood mononuclear cells (PBMCs) were taken from the interface of the samples, and washed twice with PBS. The PBMCs ($10^5$ cells/mL) were transferred to the wells of a six-well plate wherein each well contained 2 mL RPMI 1640 medium of pH 7.7.

Stimulating IFN-γ Secretion. The splenocyte or PBMC samples were co-cultured with a given amount of the Gram-positive bacteria. After the 36-hour co-culture, the cells in each sample were collected, respectively. The collected cells were re-suspended and centrifuged at 2000 rpm for 5 minutes. The supernatants were taken for the determination of IFN-γ level in each sample.

Determination of IFN-γ Level: IFN-γ Level was determined by ELISA, comprising the steps of:

adding 30 µL of 2.5 µg/mL purified mouse anti-human IFN-γ antibodies (Cat. No18181D, PharMingen®), USA) in 10 mL of coating buffer (0.1 M $Na_2HPO_4$, pH 9.0) and adding 100 µL of antibody solution into each well of a ELISA plate;

shaking the plate at 4° C.;

washing each well of the plate with washing buffer (0.05% Tween 20 in PBS);

adding 300 µL blocking buffer (1% BSA in PBS) into each well of the plate;

shaking the plate at room temperature for at least 2 hours;

adding 100 µL of the supernatant of the splenocyte sample to each well of the plate;

shaking the plate at 4° C. overnight;

washing each well of the plate with washing buffer;

adding 150 µL biotin mouse anti-human IFN-γ antibodies (Cat. No18112D, PharMingen®, USA) into each well of the plate;

incubating the plate for 1 hour at room temperature;

washing each well of the plate with washing buffer;

adding 150 µL Streptavidin-AKP diluted with dilute buffer (1:1000) into each well of the plate;

shaking the plate for 1 hour at room temperature;

washing each well of the plate with wash buffer eight times;

adding 200 µL of substrate pNpp was added into each well of the plate;

incubating the plates at room temperature until the substrate reaction is completed;

measuring the absorbance of each well of the plate at 405 nm (i.e. $OD_{405}$).

Result: Among the Gram-positive bacteria, GM-080 was selected to have the strongest ability to stimulate IFN-γ secretion in splenocyte cells and PBMCs.

EXAMPLE 2

16s rDNA Sequence Determination

DNA extraction: The genomic DNA of GM-080 and other bacteria, CCRC12913, CCRC 14001 and CCRC 16100 were extracted using QIAamp® DNA Stool Mini Kit (Qiagen®, cat No. 51504). The purification was performed according to the steps as listed below:

adding 1.4 mL of ABS buffer in to the culture and vortexing it for 1 min;

heating the solution obtained in the previous step at 70° C. for 5 min;

vortexing the solution for about 15 sec and then centrifuging it at about 13,000 rpm for 1 min;

removing the supernatant into a new centrifuge tube;

adding an InhibitEx tablet in the supernatant and shaking it to dissolve the tablet, and then incubating at room temperature for 1 min;

centrifuging the solution at about 13,000 rpm for 3 min to make the bacteria attach to InhibitEx;

removing the supernatant into a new centrifuge tube and then centrifuging at about 13,000 rpm for 3 min;

taking 200 µL of the supernatant to a new centrifuge tube and adding Protease K;

adding 200 µL of Buffer AL and vortexing it for 15 min to obtain a homogeneous solution;

adding 15 µL of Protease K into the homogenous solution and vortexing it for 15 sec;

incubating the solution at 70° C. for 10 min;

adding 200 µL of 96–100% ethanol and vortexing;

removing the solution into QIAamp spin column and centrifuging it at about 13,000 rpm for 1 min;

removing the QIAamp spin column to a new centrifuge tube and adding 500 µL Buffer AW1, and then centrifuging it at about 13,000 rpm for 1 min;

removing the QIAamp spin column to a new centrifuge tube and adding 500 µL Buffer AW2, and then centrifuging it at about 13,000 rpm for 1 min;

removing the QIAamp spin column into a new centrifuge tube and adding 200 µL Buffer AE, and then incubating it at room temperature for 1 min; and centrifuging at about 13,000 rpm for 1 min to elution DNA.

16s rDNA fragment amplification: The primers for amplifying L region were designed according to *Lactobacillus paracasei* 16S rRNA VI region, 5'- CAC CGA GAT TCA ACA TGG -3'(SEQ ID No. 1) and *Lactobacillus* conserved 16S rRNA, 5'- CCC ACT GCT GCC TCC CGT AGG AGT -3' (SEQ ID No. 2) (Ward, L. J. H. and Timmins, M. J. (1999) Differentiation of *Lactobacillus casei, Lactobacillus paracasei* and *Lactobacillus rhamnosus* by polymerase chain reaction. Lett. Appl. Microbiol. 29: 90–92). The genomic DNA of GM-080, CCRC12913, CCRC 14001 and CCRC 16100 were taken as the template for performing PCR reaction. The 16s rDNA PCR amplification program is as follows: (1) 95° C. for 10 min; (2) 95° C. for 45 sec; (3) 46° C. for 45 sec; (4) 72° C. for 1 min; (5) 72° C. for 7 min; steps 2 to 5 were repeated for 30 cycles.

16s rDNA sequence determination: The PCR products of GM-080, CCRC 12913, CCRC 14001 and CCRC 16100 were subjected to agarose gel electrophoresis (FIG. 2) and sequenced. The sequences were aligned against the multiple sequence alignment dataset (NCBI blastn, http://www.ncbi.nlm.nih.gov/BLAST) using the ARB sequence editor (release 8.1). It also showed that the 16s rDNA sequences of *Lactobacillus paracasei* strain PB4, AY186046; F31, AF243147; KLB58, AF243168 were similar to that of GM-080 as shown in FIG. 3 (generated with Vector NTI™, InforMax® Inc.). In addition, 16s rDNA phylogenetic distance tree was generated with EMBL-EBI ClustalW (http://www.ebi.ac.uk/clustalw) as shown in FIG. 4. According to the 16S rDNA analysis, GM-080 was highly related to *Lactobacillus paracasei* strain KLB58, but still distinct from KLB58. Given the above, GM-080 belonged to *Lactobacillus paracasei*.

EXAMPLE 3

Randomly Amplified Polymorphic DNA (RAPD Analysis)

DNA extraction of GM-080, *Lactobacillus paracasei* ATCC 25598, 25302, 335, 11582, and 27216 was performed as described in Example 2.

The primer for random amplification was 5'-ATG-TAACGCC-3' (Gardiner, G., Ross, R. P., Collins, J. K., Fitzgerald, G., Stanton, C. Development of a probiotic cheddar cheese containing human-derived 15 *Lactobacillus paracasei* strains. *Appl Environ Microbiol*. 1998; 64: 2192–2199).

Figure 5:
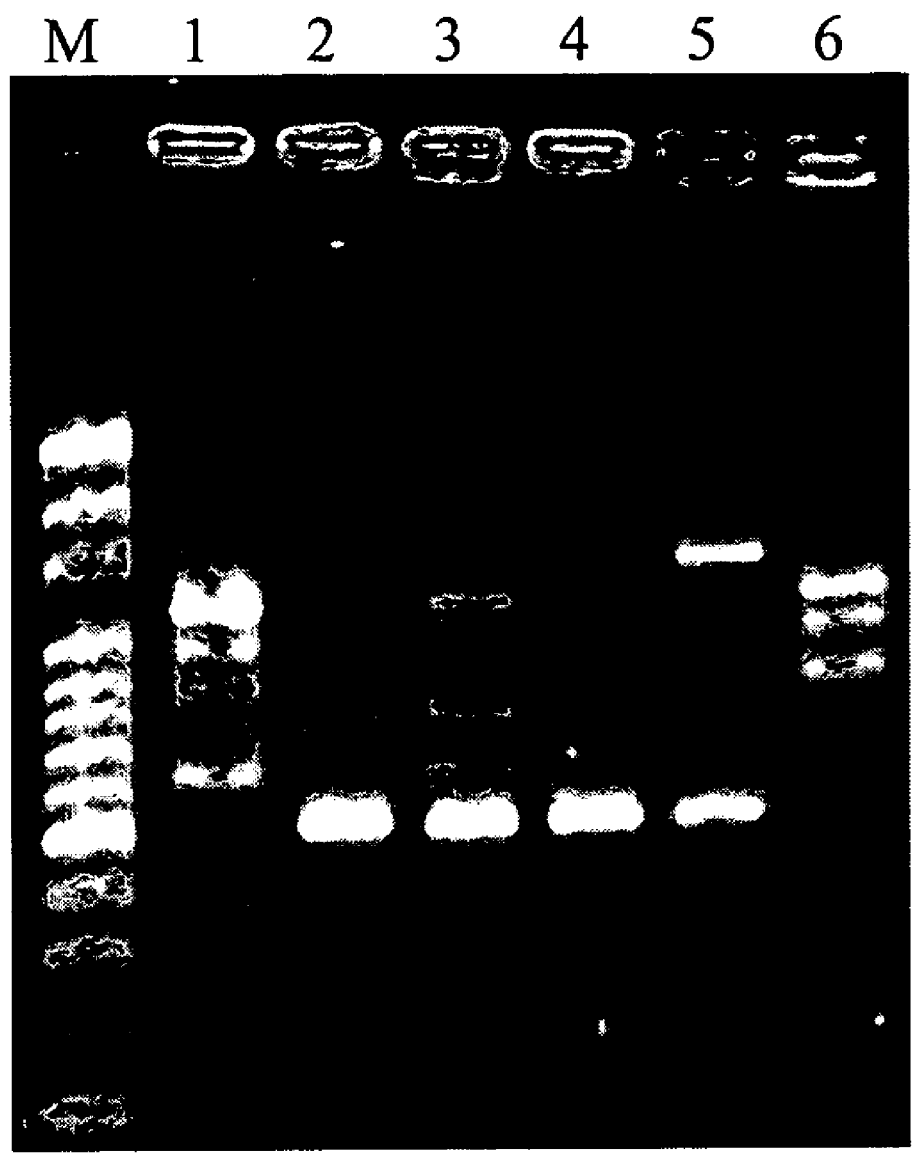
FIG. 5 illustrates the RAPD analysis of GM-080 and the conventional lactic acid bacterial strains; M: 100-bp ladders, Lane 1: GM-080; Lane 2: *Lactobacillus paracasei* ATCC 25598; Lane 3: *Lactobacillus paracasei* ATCC 25302; Lane 4: *Lactobacillus paracasei* ATCC 335; Lane 5: *Lactobacillus paracasei* ATCC 11582; Lane 6: *Lactobacillus paracasei* ATCC 27216.

The result of RAPD was shown in FIG. 5. According to the RAPD analysis, GM-080 was distinct from the conventional *Lactobacillus paracasei* strains. Given the above, GM-080 was a novel *Lactobacillus paracasei* strain.

EXAMPLE 4

Cell Wall Proteins Extraction and Analysis of GM-080

The cell wall proteins were purified according to the method described by Angelis (Angelis, M. D., Corsetti, A., Tosti, N., Rossi, J., Corbo, M. R., and Gobbetti, M. (2001) Characterization of Non-Starter Lactic Acid Bacteria from Italian Ewe Cheeses Based on Phenotypic, Genotypic, and Cell Wall Protein Analyses. *Appl. Environ. Microbiol*. 67: 2011–2020). The cells cultured overnight in MRS broth (Difco®) were harvested and then washed twice with 0.05 M Tris-HCl (pH 7.5) containing 0.1 M $CaCl_2$, and resuspended in 1 ml of the same buffer at an $OD_{600}$ of 10.0. After centrifugation at 8,000×g for 5 min, cell wall proteins were extracted from the pellets with 1.0 ml of extraction buffer (pH 8.0) containing 0.01 M EDTA, 0.01 M NaCl, and 2% (wt/vol) SDS. Suspensions were stored at room temperature for 60 min, heated at 100° C. for 5 min, and centrifuged at 11,600×g for 10 min at 4° C. The supernatants were analyzed by 12% SDS-PAGE and stained with Comassie blue.

Figure 6:
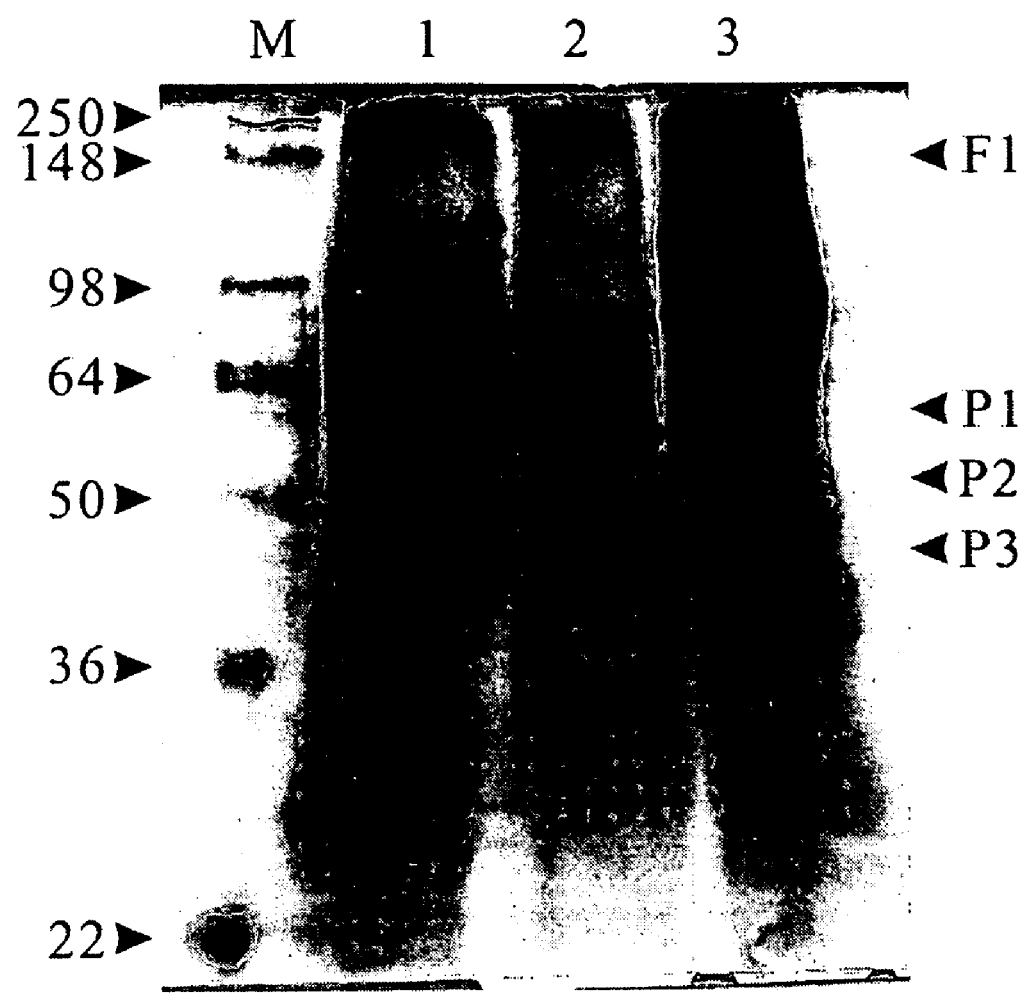
FIG. 6 illustrates the SDS-PAGE patterns of the cell wall proteins of GM-080, conventional *Lactobacillus paracasei* and *Lactobacillus fermentum* strains; wherein M represents protein molecular weight; Lane 1 represents *Lactobacillus paracasei*; Lane 2 represents *Lactobacillus paracasei* GM-080; Lane 3 represents *Lactobacillus fermentum*; F1 represents a specific band of *Lactobacillus fermentum*; and P1, P2 and P3 represent specific bands of *Lactobacillus paracasei*.

The result was shown in FIG. 6. The pattern of GM-080 had three specific bands, P1, P2 and P3 that similar to those of *Lactobacillus paracasei* reported in the prior study (Angelis et al. 2001). Therefore, GM-080 was evidenced to belong to *Lactobacillus paracasei*.

EXAMPLE 5

A Standardized Detection System for Identifying GM-080

Stimulation: The Jurkat cells were refreshed by adding a fresh medium and cultured for 16 hours. Subsequently, the cells were divided into two groups, one for the culture with the lactic acid bacteria and the other for the culture without the lactic acid bacteria. When the cell concentration reached $1 \times 10^7/10$ mL, cells were stimulated for 24 h with or without $1 \times 10^7$ different lactic acid bacteria (CCRC12193, GM-080 or CCRC12188). After stimulation, the cells were collected, washed twice with PBS, and used for RNA isolation.

RNA isolation and labeling: RNA was extracted from cell by using Trizol Reagent (Life Technologies®, Gaithersburg, Md.) according to the manufacturer's instructions. 8 L of the RNA (10 μg) and 2 L oligo poly-dT (12–18 mer, 1 g/L) were well mixed and kept at 70° C. for 10 minutes and then were cooled with ice for 2 minutes. Mixed the RNA with reverse transcription labeling mixture and 3 L Cy3-dUTP (1 mM), 2 L SuperScript III (200 U/L), and RNasin (1 L) in dark. The mixture was incubated at 50° C. for 2 hours for reverse transcription, and the reaction was terminated by adding 1.5 L 20 mM EDTA. After the labeling, RNA was removed by NaOH treatment and neutralized by HCl. cDNA was immediately purified with a YM30 purification kit.

Microarray fabrication: Hundreds of genes chosen were amplified through polymerase chain reaction and quantified by spectrophotometry at 260 nm. All purified PCR products were adjusted to a concentration of 0.1 μg/μl in 50% dimethyl sulfoxide and spotted in duplicate on UltraGAP-STM coated slides (Corning®, Inc., Coming, N. Y.). After printing, the microarrays were UV cross-link at 700 mJoule-sand stored in the slide container in a desiccator at room temperature. The genes were listed in Table 2 as mentioned above.

Microarray hybridization: Fluorescently labeled cDNA was denatured in the hybridization solution (5×SSC, 0.1% SDS and 25% formamide) at 100° C. for 5 min, cooled to ambient temperature, and deposited onto slides. The hybridization was carried out for 18 h at 55° C. After hybridization, the slides were successively washed in low-stringency (1×SSC and 0.1% SDS), medium-stringency (0.1×SSC and 0.1% SDS), high-stringency (0.1×SSC) buffer and finally were dried by compressed $N_2$.

Signal detection and data analysis: $N_2$-dried slides were immediately scanned on a GenePix 4000B scanner (Axon Instruments®), Inc.) at the same laser power and sensitivity level of the photomultiplier for each slide. Raw fluorescence data were acquired (10-nm resolution), and subsequent processing and data visualization were performed in Microsoft Excel™. In order to compare the results of independent hybridization experiments, the local background signal was subtracted from the hybridization signal of each separate spot, and then divided by the housekeeping gene, β-actin. The final expression of each gene was represented in a mean of duplicates. The gene expression profiles of the Jurkat cell cultured with and without the lactic acid bacteria were then obtained. A group of genes upregulated or down-regulated more than 2 fold in Jurkat cell cultured with lactic acid bacteria (CCRC12193, GM-080 or CCRC12188) to that cultured without the bacteria were selected. The results were shown in Table 3. The difference indicated that different species or strain can turn on or turn off different genes of the cell. Hence, from the gene expression profile, it indicated that CCRC12193, GM-080 and CCRC12188 are *L. paracusei* but belong to different strains.

EXAMPLE 6

Adhesion of GM-080 to The Epithelial Cells in The Intestine

Caco-2 cells were taken as the epithelial cells in the example. Caco-2 cells had functional microvilli and hydrolase attached thereon, it exhibited differentiated morphology and functions of a mature epithelial cell in the intestine in vitro.

Cells: Caco-2 were cultured in Mineral essential medium (MEM, GIBCO®) supplemented with 5% FBS at 37° C. in an 5% $CO_2$/95% air. For adhesion assay, 2 ml of monolayer of Caco-2 cells ($3\times10^5$ cells/ml) were prepared on glass cover slips that were placed in 6-well plate. The culture medium was replaced every second day and the monolayers were used in the adhesion assay after 2 weeks incubation. Just before use, the monolayer was wash twice with PBS and 1.5 ml of MEM was added to each well and incubated at 37° C. for 1 h before inoculation of bacteria.

Adhesion: 1.5 ml of ($4\times10^8$CFU/ml) of GM-080 washed once with PBS and resuspended in 1.5 ml MEM medium was added to the Caco-2 cells. After 1 h of incubation at 37° C., monolayer of cells were washed four times with PBS buffer, fixed with 3 ml of methanol and incubated for 5 to 10 min at room temperature, wash three times with PBS, dried in air and Gram stained. Adherent bacteria were detected microscopically under oil immersion (×100) by counting 15 random fields per coverslip and mean ±SD of adhering bacteria per field was determined.

Result: After counting, there were 102±23.6 GM-080 bacteria adhered to the Caco-2 cells. Therefore, GM-080 was regarded to have strongly adhesion to Caco-2 cells according to the standard established by Jacobsen et al. (Jacobsen, C. N., Nielsen, R. V., Hayford, A. E., Moller, P. L., Michaelsen, K. F., Paerregarrd, A., Sandstrom, B., Tvede, M. and Jakobsen, M. Screening of probiotic activities of forty-seven strains of *Lactobacillus spp.* by in vitro techniques and evaluation of the colonization ability of five selected strains in human. *Appl. Environ. Microbiol.* 1999; 65: 4949–4956).

EXAMPLE 7

Activities of GM-080 and Other Lactic Acid Bacteria in An Environment Mimicking GI Tract Acid: The overnight-cultured GM-080, *L. plantarum, L. acidophilus, L. casei*, and *L. bulgaricus* were added with 9 mL of PBS with different pH values of 2.0, 2.5 and 3.2 and then further cultured at 37° C. for 3 hours. After culturing, 1 mL cells were serially diluted with 9 mL of pH 7.4 PBS. The cell counts before and after acid treatment were estimated and shown in Table 4 as listed below.

gall. The overnight-cultured GM-080, *L. plantarum, L. acidophilus, L. casei*, and *L. bulgaricus* were added with 9 mL of PBS with different pH values of 2.0 and then further cultured at 37° C. for 3 hours. After culturing, the 1 mL cells were centrifuged at 6,000 rpm for 10 min. The pellet was re-suspended with 100 μL of PBS (pH 7.2). The solution was further added with 10 mL of MRS broth containing 0.3% (w/v) of ox gall. The cells were cultured and 1 mL of sample was taken at 3, 12 and 24 hours. The samples were serially diluted with 9 mL of pH 7.4 PBS. The cell counts before and after gall treatment were estimated and also shown in Table 4. It shows that these lactic acid bacteria remain active in the environment mimicking the GI tract.

TABLE 4

| | Cell counts (Log CFU/mL) | | |
|---|---|---|---|
| Strain | Before treatment | After treated with HCl for 3 hours | After treated with gall for 4 hours |
| L. plantarum | 9.003 | 8.114 | 7.097 |
| L. acidophilus | 9.114 | 8.097 | 8.176 |
| L. casei | 8.889 | 8.653 | 5.658 |
| GM-080 | 9.029 | 7.699 | 6.602 |
| L. bulgaricus | 9.230 | 9.076 | 7.447 |

EXAMPLE 8

Animal Model

Animals. Female BALB/c mice were obtained from the National Laboratory Animal Center in Taiwan and raised for 2 weeks in a room where light and temperature were both controlled.

Allergen purification: The dust mite allergen, Der p 5, was expressed in *Escherichia coli* comprising PGEX-2T expression vector as a recombinant Der p 5-Glutathione S-transferase fusion protein that can be purified with a glutathione-agarose binding chromatography. The specific *E. coli* strain which is able to express the desired allergen was cultured and induced. The bacteria were collected and washed with TBS (pH 7.5) and added with 0.1 M phenylmethylsulfony fluride. The cells were broken by adding DNase I, Tween 20 and lysozyme, and by freeze-thaw method. The mixed solution was added with EDTA and the residues were removed by centrifugation to obtain the supernatant containing recombinant Der p 5-Glutathione S-transferase fusion protein. The supernatant was subjected to a glutathione-agarose affinity column for absorbing the fusion protein. The column was then washed with TBS buffer at 4° C. and then with reduced glutathion in Tris base (pH 8.0) for separating the protein from column. The molecular weight of the protein was estimated by SDS-PAGE and the concentration was also assayed.

Sensitization: Mice were actively sensitized by intraperitoneal injection of 10 μg of Der p 5 with 4 mg of aluminium hydroxide. 14 and 21 days after the initial sensitization, the mice were exposed to an aerosol of 0.1% of the purified Der p 5 for 30 min to perform inhalation challenge.

Treatment: The sensitized mice were divided into three groups for the experiments. The mice of Group A were fed ten times in two weeks with MRS broth as a control group. The mice of Group B were administered with *Lactobacillus casei* ten times in two weeks and 109 CFU of bacteria were administered every time. Group B was taken as a positive control, because *L. casei* had been evidenced to be effective on inhibiting IgE secretion. The mice of Group C were administered with GM-080 ten times in two weeks and $10^9$ CFU of bacteria were administered every time.

EXAMPLE 9

IgG and IgE Secretion

Determination of Derp 5-specific IgG and IgE: Eighteen hours after last inhalation challenge, 500 μL of blood sample was taken from the tail. The blood samples were kept at room temperature for 1 hour and then subjected to centrifugation. The sera were stored at −80° C. The amounts of Der p 5-specific IgG2a, and IgE were determined by ELISA. Protein high-binding plates with 96 wells were coated with 200 μL of purified Der p 5 diluted in coating buffer (0.1 M $NaHCO_3$, pH 9.6) at a concentration of 10 μg/mL. After overnight incubation at 4° C., the plates were washed with PBS-Tween 20 and then added with 300 μL blocking buffer (3% BSA). After shaking for 2 hours at room temperature, the plates were washed again with PBS-Tween 20. Sera were used at 1:10 dilution for IgG measurement and 1:4 dilution for IgE measurement. The samples were shaken at room temperature for 2 hours. After overnight incubation at 4° C., the plates were washed with PBS-Tween 20, and added with 200 μL biotinylated rat anti-mouse IgE monoclonal antibody, or rat anti-mouse IgG mAb. The sample was shaken at room temperature for 2 hours and then washed with PBS-Tween 20. 200 μL of Streptavidin-alkaline phosphatase (1:1000) was then added and shaking the sample at room temperature for 1 h. After 6 washes, color reaction was imitated with the addition of 200 μL phosphatase substrate p-nitrophenyl phosphate, di-sodium salt (pNPP) (Sigma® N-2770, USA). Plates were read in a microplate autoreader (Metertech®, Taiwan) at 405 nm.

Statistical analysis: To assay the changes of IgE and IgG levels, repeated measures for analysis of One-way ANOVA were performed to compare the differences between the groups. After analysis of variance, Duncan multiple range tests were used to differentiate differences between experimental and control groups. A value of $p<0.05$ was used to indicate a statistically significant difference.

Figure 7:
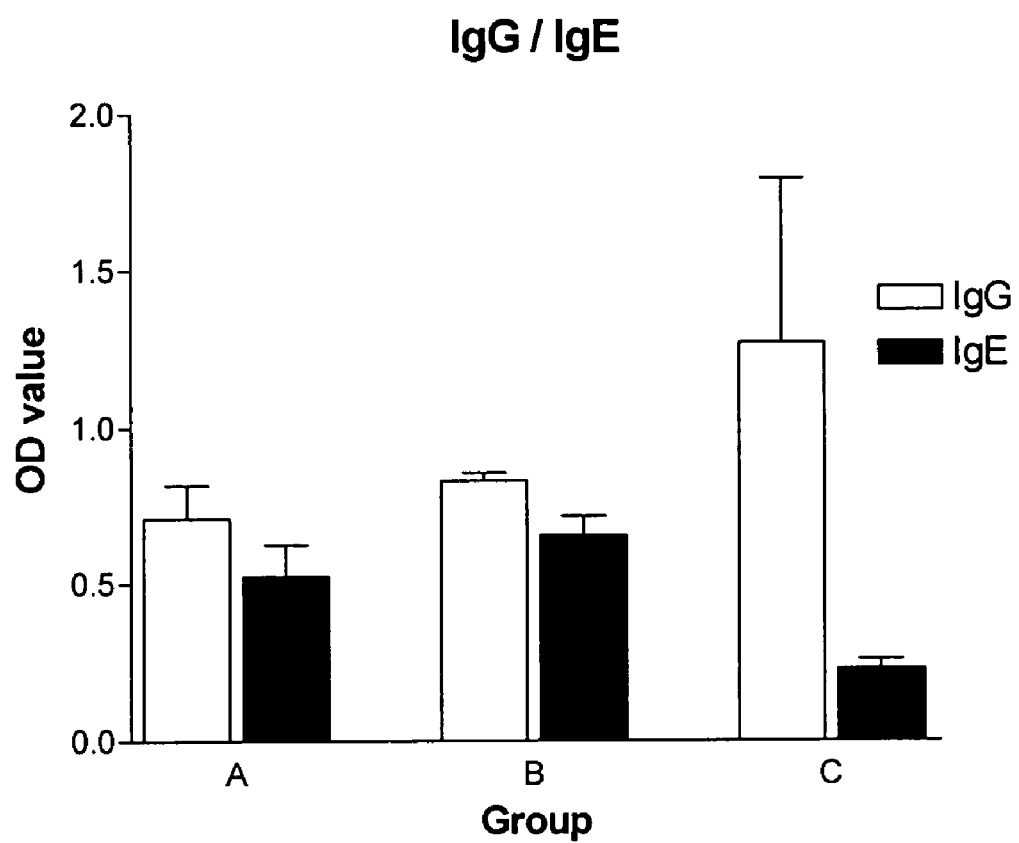
FIG. 7 illustrates Der p 5 specific IgG (white bars) and IgE (black bars) levels in serum of Der p 5-sensitized BALB/c mice challenged with inhalation Der p 5; A represents the group treated with MRS broth; B represents the group treated with *L. casei*; and C represents the group treated with GM-080.

Result. The result was shown in FIG. 7. It evidenced that IgE secretion in sera of the animal treated with GM-080 was enormously lowered and only 25% of that of without treatment. On the other hand, IgG secretion in sera of the animal treated with GM-080 was raised to two fold. Because IgG secretion represents Th1 T cell reaction, GM-080 is directed to eliminate IgE secretion that correlated to allergy related disease.

EXAMPLE 10

Bronchoalveolar Lavage Fluid Cell Count

Samples preparation: Eighteens hours after sensitization, the mice were lavaged with 5×0.5-ml aliquots of 0.9% sterile saline through a polyethylene tube introduced through a tracheostomy. Lavage fluid was centrifuged (500 g for 10 min at 4° C.), and the cell pellet was resuspended in 1 ml of PBS solution. Differentiated cell counts were made from cytospin preparations stained by Leu's stain.

Statistical analysis: To assay the changes of cell counts, repeated measures for analysis of One-way ANOVA were performed for comparing the differences between the groups. After analysis of variance, Duncan multiple range tests were used to differentiate differences between experimental and control groups. A value of $p<0.05$ was used to indicate a statistically significant difference.

Figure 8:
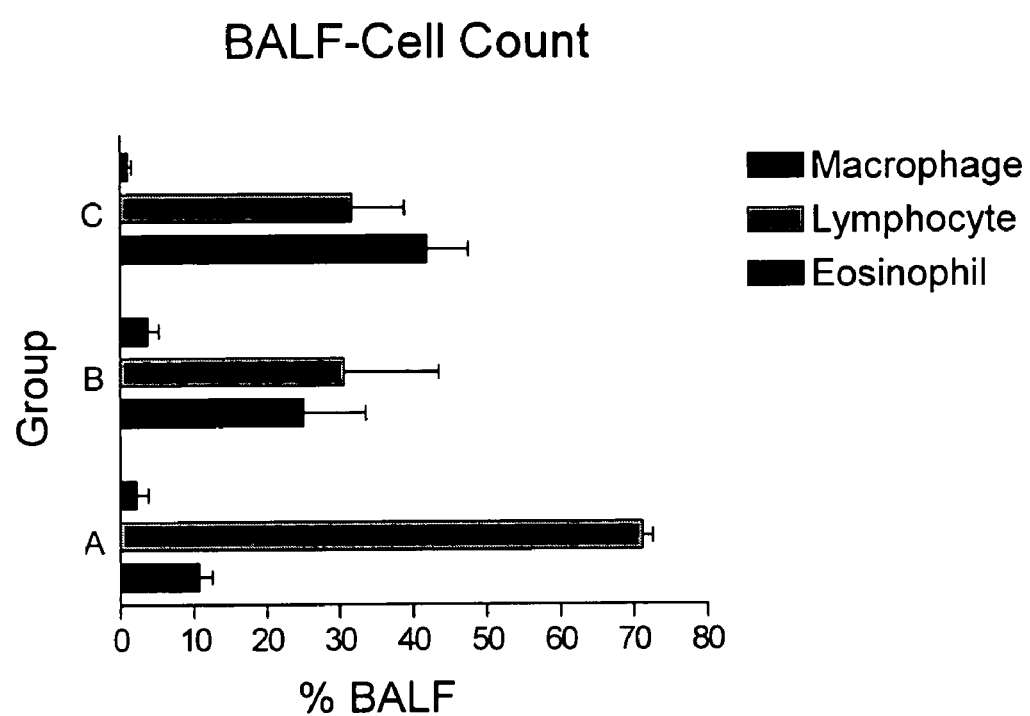
FIG. 8 illustrates the cell counts of macrophage, lymphocyte and eosinophil in the brochoalveolar lavage of Der p 5-sensitized mice; A represents the group treated with MRS broth; B represents the group treated with *L. casei*; and C represents the group treated with GM-080.

Result: The result was shown in FIG. 8. The blood cell type contribution in the BALF represents the degrees of inflammation.

Furthermore, the main symptoms of allergenic asthma are chronic inflammation in airway and eosinophils infiltration. It evidenced that the eosinophils in the BALF of the animal treated with GM-080 was enormously lowered from 5% to 1%. On the other hand, the macrophages and lymphocytes in the BALF of the animal treated with GM-080 were significantly raised.

EXAMPLE 11

IFN-γ Secretion in The Bronchoalveolar Lavage Fluid

Samples preparation: After 24 hours of sensitization, the mice were lavaged with 5×0.5-ml aliquots of 0.9% sterile saline through a polyethylene tube introduced through a tracheostomy. Lavage fluid was centrifuged (500 g for 10 min at 4° C.), and the supernatant was subjected to IFN-γ quantitative analysis as described in Example 1.

Figure 9:
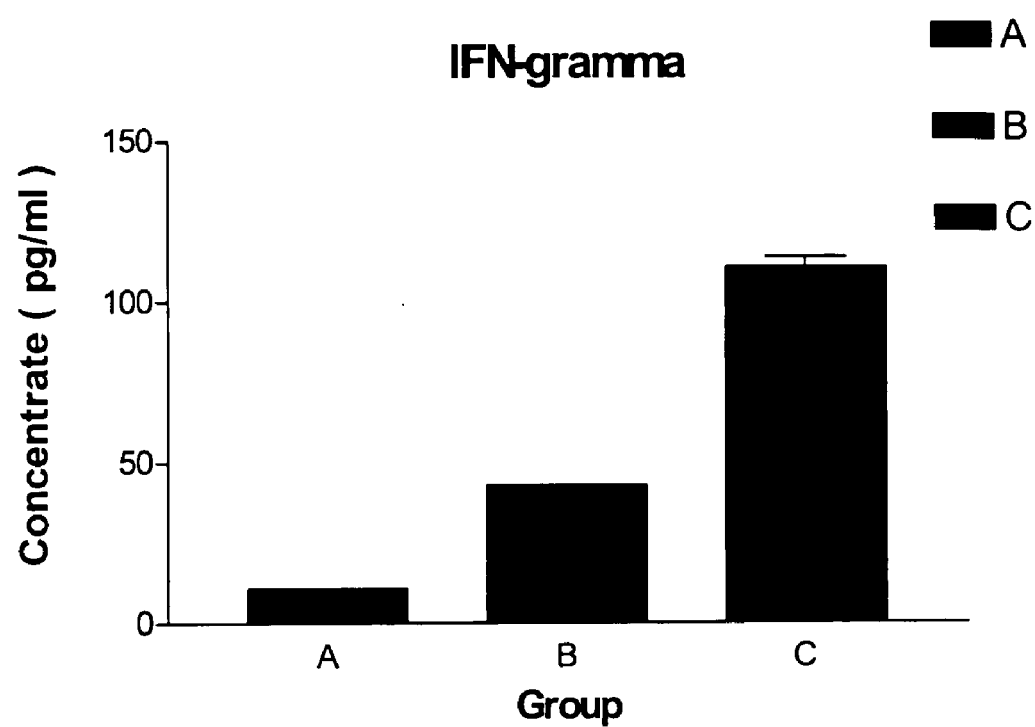
FIG. 9 illustrates the IFN-γ secretion in the brochoalveolar lavage of Der p 5-sensitized mice; A represents the group treated with MRS broth; B represents the group treated with *L. casei*; and C represents the group treated with GM-080.

Result: The result was shown in FIG. 9. It showed that the animals fed with GM-080 produced about 100 pg/mL of IFN-γ in the BALF. On the other hand, the control group produced only 20 to 40 pg/mL of IFN-γ in the BALF. GM-080 was effective on inhibiting allergenic inflammation.

EXAMPLE 12

Inactive GM-080 for Treating Allergy

Inactive GM-080 preparation: Lyophilized GM-080 powder was suspended in distilled water and autoclaved (121° C., 15 min) before feeding mice.

Mice and sensitization: Female BALB/c mice (6–8 week-old) were purchased from National Laboratory Animal Breeding and Research Center (Taipei, Taiwan). All animals were maintained individually in cages with controlled temperature (24±2° C.) and humidity (60±5%) and maintained on a 12-h light-dark cycle under specific-pathogen-free conditions. BALB/c mice were i.p. with 10 g recombinant *Dermatophagoides pteronyssinus* allergen Der p5–6×His fusion protein adsorbed to 4 mg of alumium hydroxide. The mice were fed with $10^7$, $10^9$ and $10^{11}$ CFU GM-080 per mouse per day for three weeks. The mice were boosted with the same dosage of allergen as sensitization at 14th day and were challenged with 0.1% of Der p5–6×His diluted in PBS 21 days after sensitization. The inhalation challenge was performed in 1-L chamber connected to a DeVilbiss™ pulmosonic nebulizer (Model 2512; DeVilbiss® Corp., Somerset, Pa.), which generated an aerosol mist. After 18 hours, serum was collected by tail vein bleeding and IgE was determined by ELISA as described in Example 9.

Figure 10:
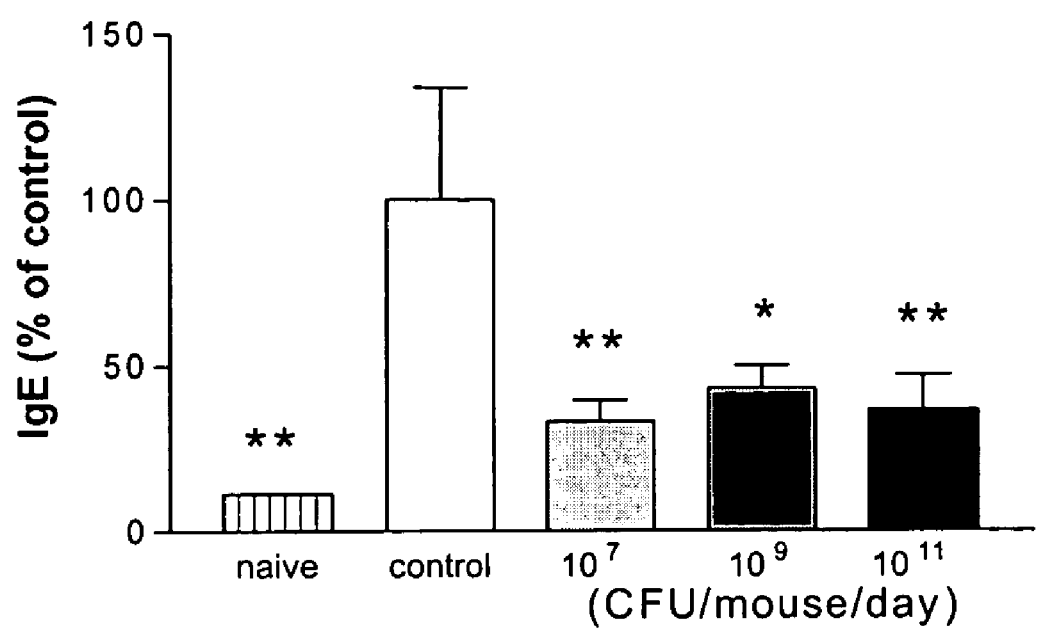
FIG. 10 illustrates the effect of inactive GM-080 on IgE production in Der p5-sensitized BALB/c mice. Der p5-sensitized mice were orally administered with different dosage of GM-080 or distilled water (control) per day for three weeks. The levels of serum Der p5-specific IgE were determined by ELISA. While comparing with the control group, *($p<0.1$) and **($p<0.05$) are significantly different by Kruskal-Wallis H test and the posteriori comparison was used by the Dunnett t Test.

Result: The result was shown in FIG. 10. It showed that BALB/c mice challenged with dust allergy Der p-5 had significantly elevated serum IgE levels compared to naive group ($p<0.05$). It suggested that allergic sensitized mice model could be successfully set up. After feeding of different dosage of GM-080 per day for 21 days, the serum IgE in GM-080 group had significantly decreased ($p<0.05$) compared with control group. The results showed that inactive GM-080 could decrease the allergic responses by reducing the allergen-specific IgE.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

What is claimed is:

1. A biologically pure microorganism, *Lactobacillus paracasei* GM-080, deposited at the China Center for Type Culture Collection under CCTCC No.: CCTCC M 204012.

2. A composition comprising the biologically pure microorganism according to claim 1 and a medium.

3. The biologically pure microorganism according to claim 1, wherein the microorganism is live.

4. The biologically pure microorganism according to claim 1, wherein the microorganism is inactivated.

5. The biologically pure microorganism according to claim 1 which is in a pharmaceutical composition, dietary supplement, food, or a component thereof.

6. An in vitro culture comprising *Lactobacillus paracasei* GM-080, deposited at the China Center for Type Culture Collection under CCTCC No.: CCTCC M 204012.

7. An in vitro culture comprising *Lactobacillus paracasei* GM-080, deposited at the China Center for Type Culture Collection under CCTCC No.: CCTCC M 204012 and one or more cells selected from the group consisting of spelenocytes and peripheral blood mononuclear cells.

8. A method for treating an allergy related disease in a subject comprising administering to said subject a composition comprising the biologically pure microorganism according to claim 1.

9. The method according to claim 8, wherein the allergy related disease is eczema.

10. The method according to claim 8, wherein the allergy related disease is atopic dermatitis.

11. The method according to claim 8, wherein the allergy related disease is allergic conjunctivitis.

12. The method according to claim 8, wherein the allergy related disease is asthma.

13. The method according to claim 8, wherein the allergy related disease is rhinitis.

14. The method according to claim 8, wherein the allergy related disease is selected from the group consisting of airway hyperreactivity and inflammation, atopic dermatitis, allergic conjunctivitis, rhinitis, sinusitis, hypersensitive pneumonia, extrinsic allergic alveolitis, urticaria, eczema, anaphylaxis, angioedema, allergic and migraine headache, certain gastrointestinal disorders, and asthma.

15. The method according to claim 14, wherein the allergy related disease is airway hyperreactivity or inflammation.

16. The method according to claim 8, wherein the allergy related disease is associated with exposure to aeroallergen.

17. The method according to claim 8, wherein the microorganism is live.

18. The method according to claim 8, wherein the microorganism is inactivated.

19. A method for stimulating IFN-γ secretion in a subject comprising administering to said subject a composition comprising the biologically pure microorganism according to claim 1.

20. The method according to claim 19, wherein the microorganism is live.

21. The method according to claim 19, wherein the microorganism is inactivated.

* * * * *